(12) United States Patent
Haubrich et al.

(10) Patent No.: US 12,733,862 B2
(45) Date of Patent: Sep. 15, 2026

(54) HYPOXIC OR ANOXIC NEUROLOGICAL INJURY DETECTION WITH EAR-WEARABLE DEVICES AND SYSTEM

(71) Applicant: Starkey Laboratories, Inc., Eden Prairie, MN (US)

(72) Inventors: Gregory John Haubrich, Champlin, MN (US); Paul Shriner, Hopkins, MN (US); Justin R. Burwinkel, Eden Prairie, MN (US); Scott Thomas Klein, Minneapolis, MN (US); David Alan Fabry, Eden Prairie, MN (US); Archelle Georgiou Feldshon, Wayzata, MN (US); Andy S. Lin, Chanhassen, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 573 days.

(21) Appl. No.: 18/019,037

(22) PCT Filed: Jul. 29, 2021

(86) PCT No.: PCT/US2021/043723

§ 371 (c)(1),
(2) Date: Jan. 31, 2023

(87) PCT Pub. No.: WO2022/026725

PCT Pub. Date: Feb. 3, 2022

(65) Prior Publication Data

US 2023/0277116 A1 Sep. 7, 2023

Related U.S. Application Data

(60) Provisional application No. 63/059,594, filed on Jul. 31, 2020.

(51) Int. Cl.
*A61B 5/00* (2006.01)
*A61B 5/024* (2006.01)
(Continued)

(52) U.S. Cl.
CPC .......... *A61B 5/4064* (2013.01); *A61B 5/4803* (2013.01); *A61B 5/6815* (2013.01);
(Continued)

(58) Field of Classification Search
CPC ... A61B 5/4064; A61B 5/4803; A61B 5/6815; A61B 5/02405; A61B 5/1101;
(Continued)

(56) References Cited

U.S. PATENT DOCUMENTS

| | | | |
|---|---|---|---|
| 8,764,651 | B2 | 7/2014 | Tran |
| 9,167,356 | B2 | 10/2015 | Higgins et al. |

(Continued)

FOREIGN PATENT DOCUMENTS

| | | |
|---|---|---|
| EP | 3376780 | 9/2018 |
| WO | 2022026725 | 2/2022 |
| WO | 2022198057 | 9/2022 |

OTHER PUBLICATIONS

Types of Aphasia, American Stroke Association (Year: 2024).*
(Continued)

*Primary Examiner* — Scott M. Getzow
(74) *Attorney, Agent, or Firm* — Pauly, De Vries Smith & Deffner LLC

(57) ABSTRACT

Embodiments herein relate to ear-wearable devices configured to detect patterns indicative of an occurrence, prodrome or sequelae of an anoxic or hypoxic neurological injury. In an embodiment, an ear-wearable device is included. The ear-wearable device can be configured to monitor signals from a microphone and/or a motion sensor to detect a pattern or patterns indicative of an occurrence of an anoxic or
(Continued)

hypoxic neurological injury. In some embodiments, a method of monitoring an ear-wearable device wearer for an occurrence of an anoxic or hypoxic neurological injury is included. The method can include gathering signals from one or more of a microphone, a motion sensor, or another sensor of an ear-wearable device and monitoring the signals to detect a pattern or patterns indicative of an occurrence of an anoxic or hypoxic neurological injury. Other embodiments are also included herein.

17 Claims, 12 Drawing Sheets

(51) Int. Cl.
*A61B 5/11* (2006.01)
*A61B 5/361* (2021.01)

(52) U.S. Cl.
CPC ......... *A61B 5/02405* (2013.01); *A61B 5/1101* (2013.01); *A61B 5/1123* (2013.01); *A61B 5/361* (2021.01); *A61B 5/4839* (2013.01)

(58) Field of Classification Search
CPC ..... A61B 5/1123; A61B 5/361; A61B 5/4839; A61B 5/0077
See application file for complete search history.

(56) References Cited

U.S. PATENT DOCUMENTS 9,210,518 B2 12/2015 Zhang
9,219,964 B2 12/2015 Merks
9,848,273 B1 12/2017 Helwani et al.
11,055,575 B2 7/2021 Anushiravani et al.
2003/0036041 A1 2/2003 Evangelisti
2008/0001735 A1* 1/2008 Tran ....................... A61B 8/565 340/539.22
2008/0146892 A1* 6/2008 LeBoeuf ............. A61B 5/4812 600/300
2015/0118661 A1 4/2015 Haruta et al.
2017/0007167 A1* 1/2017 Kostic .................. A61B 5/6898
2017/0095202 A1 4/2017 Facteau et al.
2017/0258389 A1 9/2017 Howard
2019/0029588 A1 1/2019 Weffers-Albu
2019/0304329 A1* 10/2019 Webb .................... A63F 9/0001
2020/0143703 A1 5/2020 Fabry et al.
2020/0236479 A1 7/2020 Burwinkel et al.
2020/0268315 A1 8/2020 Burwinkel et al.
2021/0037867 A1 2/2021 Tristram et al.
2022/0301685 A1 9/2022 Burwinkel et al.

OTHER PUBLICATIONS

"International Preliminary Report on Patentability", for PCT Application No. PCT/US2022/020966 mailed Sep. 28, 2023 (12 pages).
"International Preliminary Report on Patentability," for PCT Application No. PCT/US2021/043723 mailed Feb. 9, 2023 (9 pages).
"International Search Report and Written Opinion," for PCT Application No. PCT/US2021/043723 mailed Nov. 12, 2021 (13 pages).
"International Search Report and Written Opinion," for PCT Application No. PCT/US2022/020966 mailed Sep. 6, 2022 (19 pages).
"Invitation to Pay Additional Fees," for PCT Application No. PCT/US2022/020966 mailed Jul. 15, 2022 (12 pages).
"Non-Final Office Action," for U.S. Appl. No. 17/698,677 mailed May 7, 2026 (34 pages).

* cited by examiner

HYPOXIC OR ANOXIC NEUROLOGICAL INJURY DETECTION WITH EAR-WEARABLE DEVICES AND SYSTEM

This application is being filed as a PCT International Patent application on Jul. 29, 2021 in the name of Starkey Laboratories, Inc., a U.S. national corporation, applicant for the designation of all countries, and Gregory John Haubrich, a U.S. Citizen, and Paul Shriner, a U.S. Citizen, and Justin R. Burwinkel, a U.S. Citizen, and Scott Thomas Klein, a U.S. Citizen, and David Alan Fabry, a U.S. Citizen, and Archelle Georgiou, a U.S. Citizen, and Andy S. Lin, a U.S. Citizen, inventors and applicants for the designation of all countries, and claims priority to U.S. Provisional Patent Application No. 63/059,594, filed Jul. 31, 2020, the contents of which are herein incorporated by reference in its entirety.

FIELD

Embodiments herein relate to ear-wearable devices configured to detect patterns indicative of one or more of an occurrence, prodrome or sequelae of an anoxic or hypoxic neurological injury and related systems and methods.

BACKGROUND

Cerebral hypoxia is a condition in which the brain is deprived of sufficient oxygen. Cerebral anoxia is a condition in which the brain is completely deprived of oxygen. Prolonged hypoxia or anoxia induces neuronal cell death via apoptosis, resulting in a hypoxic brain injury.

Unfortunately, hypoxic-anoxic injuries are quite common. One such type of hypoxic-anoxic injury is a stroke. It is estimated that one in four people over the age of 25 is at risk of stroke in their lifetime, and that over 15,000,000 strokes occur worldwide each year. Of these cases, roughly 15% of the victims expire shortly after the stroke and another 50% become permanently disabled. As such, stroke is a leading cause of serious long-term disability.

Approximately 85-90% of strokes are ischemic wherein a vascular blockage (i.e., infarct) occurs in a cerebral artery due to a thrombus (a clot that forms in the cerebral artery) or embolism (a clot that forms outside the brain, such as in the heart, and is then carried to the brain) within the artery. The remainder of strokes are hemorrhagic. A hemorrhagic stroke is a stroke that follows from hemorrhage or bleeding in the brain. Beyond strokes, a similar event is a transient ischemic attack (TIA). A transient ischemic attack can be caused by the same conditions that cause an ischemic stroke, but the blockage is temporary.

Early therapeutic intervention is important for treating virtually all forms of hypoxic-anoxic injury associated with cerebral insults such as strokes and the like. For example, if administered within three hours of an ischemic stroke, tissue plasminogen activator can dissolve blood clots and thereby improve blood flow and improving the chances of recovering from a stroke. Unfortunately, the individual suffering the stroke may not recognize what they are experiencing and/or may not be in a condition to seek assistance independently. As such, it can be difficult for some individuals to receive a timely therapeutic intervention.

SUMMARY

Embodiments herein relate to ear-wearable devices configured to detect patterns indicative of one or more of an occurrence, prodrome or sequelae of an anoxic or hypoxic neurological injury and related systems and methods.

In a first aspect, an ear-wearable device is included having a control circuit, a microphone in electrical communication with the control circuit, a motion sensor in electrical communication with the control circuit, and a power supply circuit in electrical communication with the control circuit. The ear-wearable device can be configured to monitor signals from the microphone and/or the motion sensor to detect a pattern or patterns indicative of an occurrence of an anoxic or hypoxic neurological injury.

In a second aspect, in addition to one or more of the preceding or following aspects, or in the alternative to some aspects, the pattern can include the content of an ear-wearable device wearer's speech.

In a third aspect, in addition to one or more of the preceding or following aspects, or in the alternative to some aspects, the pattern can include words indicating confusion.

In a fourth aspect, in addition to one or more of the preceding or following aspects, or in the alternative to some aspects, the pattern can include speech patterns of an ear-wearable device wearer's speech.

In a fifth aspect, in addition to one or more of the preceding or following aspects, or in the alternative to some aspects, the pattern can include long delays.

In a sixth aspect, in addition to one or more of the preceding or following aspects, or in the alternative to some aspects, the pattern can include the clarity of an ear-wearable device wearer's speech.

In a seventh aspect, in addition to one or more of the preceding or following aspects, or in the alternative to some aspects, wherein clarity includes at least one of breathiness, pitch change, vowel instability, and roughness.

In an eighth aspect, in addition to one or more of the preceding or following aspects, or in the alternative to some aspects, the pattern can include slurred words.

In a ninth aspect, in addition to one or more of the preceding or following aspects, or in the alternative to some aspects, the pattern can include changed pronunciation.

In a tenth aspect, in addition to one or more of the preceding or following aspects, or in the alternative to some aspects, wherein the pattern is indicative of motor impairment.

In an eleventh aspect, in addition to one or more of the preceding or following aspects, or in the alternative to some aspects, wherein the pattern is indicative of a sudden decrease in coordination.

In a twelfth aspect, in addition to one or more of the preceding or following aspects, or in the alternative to some aspects, wherein the pattern is indicative of onset of dizziness or imbalance.

In a thirteenth aspect, in addition to one or more of the preceding or following aspects, or in the alternative to some aspects, wherein the ear-wearable device is configured to detect a non-volitional body movement.

In a fourteenth aspect, in addition to one or more of the preceding or following aspects, or in the alternative to some aspects, wherein the ear-wearable device is configured to detect an essential tremor on the face or body.

In a fifteenth aspect, in addition to one or more of the preceding or following aspects, or in the alternative to some aspects, wherein the ear-wearable device is configured to detect a non-volitional eye movement.

In a sixteenth aspect, in addition to one or more of the preceding or following aspects, or in the alternative to some aspects, wherein the ear-wearable device is configured to query an ear-wearable device wearer if a pattern indicative of an occurrence of an anoxic or hypoxic neurological injury is detected.

In a seventeenth aspect, in addition to one or more of the preceding or following aspects, or in the alternative to some aspects, wherein the ear-wearable device is configured to evaluate a nature or quality of a response from the ear-wearable device wearer in response to the query.

In an eighteenth aspect, in addition to one or more of the preceding or following aspects, or in the alternative to some aspects, wherein the ear-wearable device is configured to prompt the ear-wearable device wearer to look at an accessory device equipped with a camera if a pattern indicative of an occurrence of an anoxic or hypoxic neurological injury is detected.

In a nineteenth aspect, in addition to one or more of the preceding or following aspects, or in the alternative to some aspects, the pattern can include eye dilation.

In a twentieth aspect, in addition to one or more of the preceding or following aspects, or in the alternative to some aspects, the pattern can include non-volitional eye movement.

In a twenty-first aspect, in addition to one or more of the preceding or following aspects, or in the alternative to some aspects, the pattern can include face droop.

In a twenty-second aspect, in addition to one or more of the preceding or following aspects, or in the alternative to some aspects, wherein the query includes a prompt to execute a movement protocol.

In a twenty-third aspect, in addition to one or more of the preceding or following aspects, or in the alternative to some aspects, the device further can include a cardiac sensor, wherein the ear-wearable device is configured to identify a cardiac pattern indicative of an occurrence of an anoxic or hypoxic neurological injury.

In a twenty-fourth aspect, in addition to one or more of the preceding or following aspects, or in the alternative to some aspects, the cardiac pattern can include atrial fibrillation.

In a twenty-fifth aspect, in addition to one or more of the preceding or following aspects, or in the alternative to some aspects, the cardiac pattern can include beat variability.

In a twenty-sixth aspect, in addition to one or more of the preceding or following aspects, or in the alternative to some aspects, wherein the ear-wearable device is configured to generate an alert if an occurrence of an anoxic or hypoxic neurological injury is detected.

In a twenty-seventh aspect, in addition to one or more of the preceding or following aspects, or in the alternative to some aspects, wherein the alert is generated according to a tiered alert classification.

In a twenty-eighth aspect, in addition to one or more of the preceding or following aspects, or in the alternative to some aspects, wherein the ear-wearable device is configured to initiate the administration of a therapy if a pattern of an occurrence of an anoxic or hypoxic neurological injury is detected.

In a twenty-ninth aspect, in addition to one or more of the preceding or following aspects, or in the alternative to some aspects, wherein initiating the administration of a therapy includes sending a command to a drug delivery device.

In a thirtieth aspect, in addition to one or more of the preceding or following aspects, or in the alternative to some aspects, the therapy can include at least one of streptokinase and tissue plasminogen activator.

In a thirty-first aspect, in addition to one or more of the preceding or following aspects, or in the alternative to some aspects, wherein the ear-wearable device is configured to mark the time of first detection of a pattern indicative of an occurrence of an anoxic or hypoxic neurological injury and subsequently transmit the same for receipt by a care provider.

In a thirty-second aspect, a hearing assistance system is included having an accessory device. The accessory device can include a control circuit, a microphone, in electrical communication with the control circuit, a motion sensor in electrical communication with the control circuit, and a power supply in electrical communication with the control circuit. The accessory device can be configured to monitor signals from the microphone and/or the motion sensor to detect a pattern or patterns indicative of an occurrence of an anoxic or hypoxic neurological injury.

In a thirty-third aspect, in addition to one or more of the preceding or following aspects, or in the alternative to some aspects, the accessory device can be configured to receive signals from an ear-wearable device including signals derived from a microphone and a motion sensor, monitor the signals from the ear-wearable device, and detect patterns indicative of an occurrence of an anoxic or hypoxic neurological injury.

In a thirty-fourth aspect, in addition to one or more of the preceding or following aspects, or in the alternative to some aspects, the pattern can include the content of an ear-wearable device wearer's speech.

In a thirty-fifth aspect, in addition to one or more of the preceding or following aspects, or in the alternative to some aspects, the pattern can include words indicating confusion.

In a thirty-sixth aspect, in addition to one or more of the preceding or following aspects, or in the alternative to some aspects, the pattern can include speech patterns of an ear-wearable device wearer's speech.

In a thirty-seventh aspect, in addition to one or more of the preceding or following aspects, or in the alternative to some aspects, the pattern can include long delays.

In a thirty-eighth aspect, in addition to one or more of the preceding or following aspects, or in the alternative to some aspects, the pattern can include the clarity of an ear-wearable device wearer's speech.

In a thirty-ninth aspect, in addition to one or more of the preceding or following aspects, or in the alternative to some aspects, wherein clarity includes at least one of breathiness, pitch change, vowel instability, and roughness.

In a fortieth aspect, in addition to one or more of the preceding or following aspects, or in the alternative to some aspects, the pattern can include slurred words.

In a forty-first aspect, in addition to one or more of the preceding or following aspects, or in the alternative to some aspects, the pattern can include changed pronunciation.

In a forty-second aspect, in addition to one or more of the preceding or following aspects, or in the alternative to some aspects, wherein the pattern is indicative of motor impairment.

In a forty-third aspect, in addition to one or more of the preceding or following aspects, or in the alternative to some aspects, wherein the pattern is indicative of a sudden decrease in coordination.

In a forty-fourth aspect, in addition to one or more of the preceding or following aspects, or in the alternative to some aspects, wherein the pattern is indicative of onset of dizziness or imbalance.

In a forty-fifth aspect, in addition to one or more of the preceding or following aspects, or in the alternative to some aspects, wherein the hearing assistance system is configured to detect a non-volitional body movement.

In a forty-sixth aspect, in addition to one or more of the preceding or following aspects, or in the alternative to some aspects, wherein the hearing assistance system is configured to detect an essential tremor on the face or body.

In a forty-seventh aspect, in addition to one or more of the preceding or following aspects, or in the alternative to some aspects, wherein the hearing assistance system is configured to detect a non-volitional eye movement.

In a forty-eighth aspect, in addition to one or more of the preceding or following aspects, or in the alternative to some aspects, wherein the hearing assistance system is configured to prompt an ear-wearable device wearer if a pattern indicative of an occurrence of an anoxic or hypoxic neurological injury is detected.

In a forty-ninth aspect, in addition to one or more of the preceding or following aspects, or in the alternative to some aspects, wherein the hearing assistance system is configured to evaluate a nature or quality of a response from the ear-wearable device wearer in response to the query.

In a fiftieth aspect, in addition to one or more of the preceding or following aspects, or in the alternative to some aspects, the accessory device can include a camera.

In a fifty-first aspect, in addition to one or more of the preceding or following aspects, or in the alternative to some aspects, wherein the hearing assistance system is configured to prompt the ear-wearable device wearer to look at the camera if a pattern indicative of an occurrence of an anoxic or hypoxic neurological injury is detected.

In a fifty-second aspect, in addition to one or more of the preceding or following aspects, or in the alternative to some aspects, wherein the hearing assistance system is configured to evaluate a nature or quality of a response from an ear-wearable device wearer in response to the query.

In a fifty-third aspect, in addition to one or more of the preceding or following aspects, or in the alternative to some aspects, wherein the hearing assistance system is configured to initiate the administration of a therapy if a pattern of an occurrence of an anoxic or hypoxic neurological injury is detected.

In a fifty-fourth aspect, in addition to one or more of the preceding or following aspects, or in the alternative to some aspects, wherein initiating the administration of a therapy includes sending a command to a drug delivery device.

In a fifty-fifth aspect, in addition to one or more of the preceding or following aspects, or in the alternative to some aspects, the therapy can include at least one of streptokinase and tissue plasminogen activator.

In a fifty-sixth aspect, a method of monitoring an ear-wearable device wearer for an occurrence of an anoxic or hypoxic neurological injury is included, the method including gathering signals from one or more of a microphone, a motion sensor, or another sensor of an ear-wearable device, and monitoring the signals to detect a pattern or patterns indicative of an occurrence of an anoxic or hypoxic neurological injury.

In a fifty-seventh aspect, in addition to one or more of the preceding or following aspects, or in the alternative to some aspects, the pattern can include the content of the ear-wearable device wearer's speech.

In a fifty-eighth aspect, in addition to one or more of the preceding or following aspects, or in the alternative to some aspects, the pattern can include words indicating confusion.

In a fifty-ninth aspect, in addition to one or more of the preceding or following aspects, or in the alternative to some aspects, the pattern can include speech patterns of the ear-wearable device wearer's speech.

In a sixtieth aspect, in addition to one or more of the preceding or following aspects, or in the alternative to some aspects, the pattern can include long delays.

In a sixty-first aspect, in addition to one or more of the preceding or following aspects, or in the alternative to some aspects, the pattern can include the clarity of the ear-wearable device wearer's speech.

In a sixty-second aspect, in addition to one or more of the preceding or following aspects, or in the alternative to some aspects, wherein clarity includes at least one of breathiness, pitch change, vowel instability, and roughness.

In a sixty-third aspect, in addition to one or more of the preceding or following aspects, or in the alternative to some aspects, the pattern can include slurred words.

In a sixty-fourth aspect, in addition to one or more of the preceding or following aspects, or in the alternative to some aspects, the pattern can include changed pronunciation.

In a sixty-fifth aspect, in addition to one or more of the preceding or following aspects, or in the alternative to some aspects, the pattern can include slurred words.

In a sixty-sixth aspect, in addition to one or more of the preceding or following aspects, or in the alternative to some aspects, wherein the pattern is indicative of motor impairment.

In a sixty-seventh aspect, in addition to one or more of the preceding or following aspects, or in the alternative to some aspects, wherein the pattern is indicative of a sudden decrease in coordination.

In a sixty-eighth aspect, in addition to one or more of the preceding or following aspects, or in the alternative to some aspects, wherein the pattern is indicative of onset of dizziness or imbalance.

In a sixty-ninth aspect, in addition to one or more of the preceding or following aspects, or in the alternative to some aspects, the method further can include querying the device wearer if a pattern indicative of an occurrence of an anoxic or hypoxic neurological injury is detected.

In a seventieth aspect, in addition to one or more of the preceding or following aspects, or in the alternative to some aspects, the method further can include prompting the device wearer to look at an accessory device equipped with a camera if a pattern indicative of an occurrence of an anoxic or hypoxic neurological injury is detected.

In a seventy-first aspect, in addition to one or more of the preceding or following aspects, or in the alternative to some aspects, the pattern can include eye dilation.

In a seventy-second aspect, in addition to one or more of the preceding or following aspects, or in the alternative to some aspects, the pattern can include non-volitional eye movement.

In a seventy-third aspect, in addition to one or more of the preceding or following aspects, or in the alternative to some aspects, the pattern can include face droop.

In a seventy-fourth aspect, in addition to one or more of the preceding or following aspects, or in the alternative to some aspects, wherein the query includes a prompt to execute a movement protocol.

In a seventy-fifth aspect, in addition to one or more of the preceding or following aspects, or in the alternative to some aspects, the method further can include identifying a cardiac pattern indicative of an occurrence of an anoxic or hypoxic neurological injury.

In a seventy-sixth aspect, in addition to one or more of the preceding or following aspects, or in the alternative to some aspects, the cardiac pattern can include atrial fibrillation.

In a seventy-seventh aspect, in addition to one or more of the preceding or following aspects, or in the alternative to some aspects, the cardiac pattern can include beat variability.

In a seventy-eighth aspect, in addition to one or more of the preceding or following aspects, or in the alternative to some aspects, the method further can include generating an alert if an occurrence of an anoxic or hypoxic neurological injury is detected.

In a seventy-ninth aspect, in addition to one or more of the preceding or following aspects, or in the alternative to some aspects, wherein the alert is generated according to a tiered alert classification.

In an eightieth aspect, in addition to one or more of the preceding or following aspects, or in the alternative to some aspects, the method further can include marking the time of first detection of a pattern indicative of an occurrence of an anoxic or hypoxic neurological injury and subsequently transmitting the same for receipt by a care provider.

In an eighty-first aspect, in addition to one or more of the preceding or following aspects, or in the alternative to some aspects, the method further can include detecting a non-volitional body movement.

In an eighty-second aspect, in addition to one or more of the preceding or following aspects, or in the alternative to some aspects, can include an essential tremor on the face or body.

In an eighty-third aspect, in addition to one or more of the preceding or following aspects, or in the alternative to some aspects, the method further can include detecting a non-volitional eye movement.

In an eighty-fourth aspect, in addition to one or more of the preceding or following aspects, or in the alternative to some aspects, the method further can include initiating the administration of a therapy if a pattern of an occurrence of an anoxic or hypoxic neurological injury is detected.

In an eighty-fifth aspect, in addition to one or more of the preceding or following aspects, or in the alternative to some aspects, wherein initiating the administration of a therapy includes sending a command to a drug delivery device.

In an eighty-sixth aspect, in addition to one or more of the preceding or following aspects, or in the alternative to some aspects, the therapy can include at least one of streptokinase and tissue plasminogen activator.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, hypoxic-anoxic injuries are quite common and very serious. For example, strokes (ischemic and hemorrhagic) have high rates of mortality and extremely high rates of sequalae. Unfortunately, the individual suffering a neurological injury (e.g., a stroke) may not recognize what they are experiencing and/or may not be in a condition to seek assistance independently.

In accordance with embodiments herein, ear-wearable devices can be used in order to rapidly identify the onset of a hypoxic-anoxic neurological insult and/or resulting injury such as a stroke. In specific, ear-wearable devices described herein can include sensors such as microphones, motion sensors, and others and can monitor signals from these sensors so as to quickly identify the onset, prodrome, or sequelae of a possible hypoxic-anoxic neurological injury and, in some embodiments, send an alert in order to request medical assistance. For example, ear-wearable devices herein can monitor signals from microphones in order to detect changes in the speech-language (a broad scope of speech, language, literacy, swallowing, and voice issues involved in communication) of the device wearer and determine that they are characteristic of hypoxic-anoxic neurological injury (e.g., aphasia, voice difficulties, roughness, breathiness, articulation, vowel instability, word finding and other semantic issues, atypical pragmatics, literacy impairments, and the like).

Further, ear-wearable devices herein can monitor signals from a motion sensor in order to detect patterns of movement (e.g., fasciculation-like, shivering, jerky, tonic-clonic, and intermittent shaking movements) or the lack thereof that are characteristic of hypoxic-anoxic neurological injury.

Figure 1:
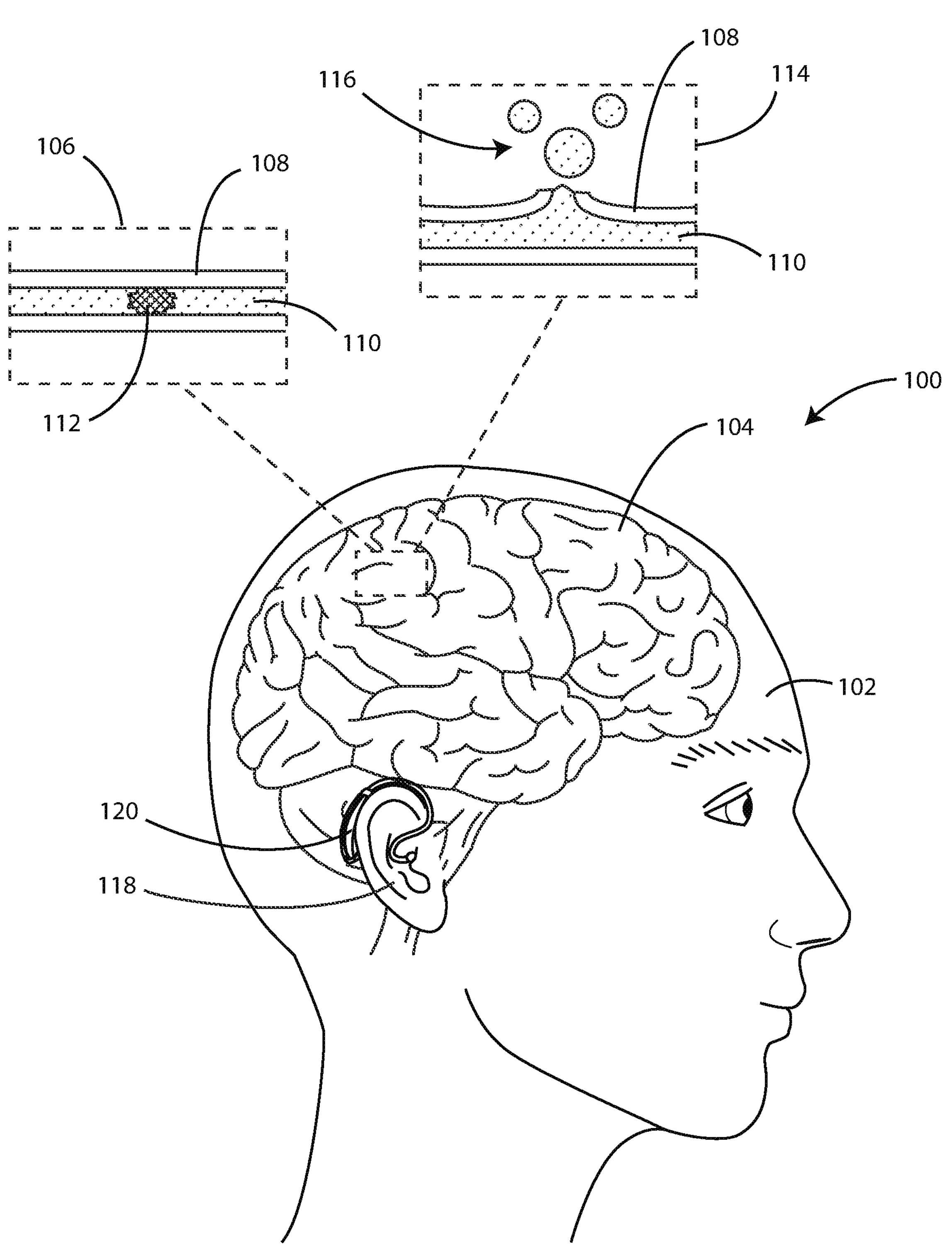
FIG. 1 is a schematic view of an ear-wearable device and wearer in accordance with various embodiments herein.

Referring now to FIG. 1, a schematic view of an ear-wearable device 120 and device wearer 100. Also shown is the head 102, brain 104, and an ear 118 of the device wearer 100.

FIG. 1 shows an ischemic stroke 106 and a hemorrhagic stroke 114. The brain 104 includes a cerebral artery 108 and blood 110 therein. It will be appreciated that while a cerebral artery 108 is depicted in FIG. 1, this could also apply to other portions of an individual's intracranial vascularization. In the case of the ischemic stroke 106, the cerebral artery 108 also includes a thrombus 112. In the case of the hemorrhagic stroke 114, the cerebral artery 108 is breached leading to hemorrhage 116.

In various embodiments, the ear-wearable device 120 is configured to monitor signals from a microphone, a motion sensor, or other sensors or inputs to detect patterns indicative of an occurrence, prodrome, or sequelae of an anoxic or hypoxic neurological insult/injury. Exemplary patterns are described in greater detail below. In various embodiments, an ear-wearable device 120 can include various components (described in greater detail below) such as a control circuit, a microphone, a motion sensor, and a power supply circuit.

If a pattern indicative of an occurrence, prodrome, or sequelae of an anoxic or hypoxic neurological injury is detected, then the device or system can take various actions. In some embodiments, the device or system can take actions to confirm that the detected pattern actually represents an occurrence, prodrome, or sequelae of an anoxic or hypoxic neurological injury. This confirmation can be performed in various ways. In some embodiments, the ear-wearable device 120 is configured to query the device wearer 100 if a pattern indicative of one or more of an occurrence, prodrome or sequelae of an anoxic or hypoxic neurological injury is detected. In some embodiments, the query can take the form of a simple question or series of questions. In some embodiments, the query can take the form of a request for the device wearer 100 to do something. Depending on the response to the query (explicit response or observed response), the system can take appropriate responsive action.

In some embodiments, if a pattern consistent with an anoxic or hypoxic neurological insult/injury is detected, the device or system can start a time clock period (or "cautionary period") wherein it continues to evaluate signals and/or inputs for a recurrence of a pattern consistent with an anoxic or hypoxic neurological insult/injury to serve as confirmation. In some cases, if the pattern is detected again within the time clock period, then the system or device can confirm that an anoxic or hypoxic insult/injury is indicated and take some type of corrective action. However, if the pattern is not detected again, then in some embodiments the event is logged, but no action is taken. For example, if the first detected pattern represents an actual incidence of anoxic or hypoxic insult/injury, then it would generally be expected that the pattern will recur. On the contrary, if the detected pattern is spurious, then it would be expected that the pattern would not recur. As such, by continuing to monitor signals during this time clock period, then the device can confirm whether or not an anoxic or hypoxic neurological injury is actually taking place. The time clock period can vary. In some embodiments, the time clock period can be about 1, 2, 3, 4, 5, 6, 7, 8, 10, 15, 20, 30 or 60 minutes or an amount of time falling within a range between any of the foregoing.

In some cases, the system or device may cut short or abbreviate the time clock period if patterns are detected sufficient to make waiting the rest of the time clock period unnecessary. For example, if a different type of pattern is detected that is also indicative of a neurological injury (e.g., an initial pattern is identified by evaluating signals from a motion sensor indicating a sudden loss of coordination and, simultaneously or sequentially, evaluation of the device-wearer's speech-language indicates confusion) then the time clock period can be cut short and corrective actions can be taken immediately. In such a scenario, the use of multiple sensors and/or inputs to assist in identifying a neurological injury can improve efficiency and accuracy and reduce the amount of time that elapses before a corrective action is initiated. In some embodiments, the system or device can cut short or abbreviate the time clock period if one or more patterns are identified that generates a high confidence that a neurological insult/injury has taken place.

It will be appreciated that one or more of an expressive and a receptive speech-language deficiency may be present in association with a cerebral insult and the same can be identified herein.

Corrective actions (or responsive actions) herein can take on many different forms. In various embodiments, the ear-wearable device 120 is configured to generate an alert if an occurrence, prodrome or sequelae of an anoxic or hypoxic neurological injury is detected. Alerts can take on various forms. In some embodiments, the alert can be an electronic message to a third party or a system where a third party can receive the electronic message. In some embodiments, the alert can be a message delivered to emergency first responders. In some embodiments, the corrective action can take the form of initiating a call to an emergency service such as 911 or the like.

In some embodiments, an alert can be generated according to a tiered alert classification. The tiered alert classification can include various levels of perceived neurological injury severity and/or certainty thereof. In some embodiments, the levels can include severe, moderate, and mild. Because the timing for treatment after neurological injury occurs can be critical, in various embodiments, the ear-wearable device 120 wherein the ear-wearable device 120 is configured to mark the time of first detection of a pattern indicative of an occurrence, prodrome or sequelae of an anoxic or hypoxic neurological injury and subsequently transmit the same for receipt by a care provider.

As described above, it is critical that an individual suffering from an anoxic or hypoxic neurological injury is treated as quickly as possible. In some embodiments, devices or systems herein can be configured to initiate the administration of a therapy if a pattern of an occurrence of an anoxic or hypoxic neurological injury is detected. In some embodiments, such actions can be taken if the device or system determines that the neurological injury is severe according to a tiered alert classification. In some cases, initiating the administration of a therapy can include sending or issuing a command to a drug delivery device. For example, a suitable drug-delivery device could include an implanted drug delivery device, a skin-mounted or transdermal drug delivery device, an external drug delivery device, or the like. In some cases, a drug delivery device can be a part of the ear-worn device system. In some embodiments, initiating the administration of a therapy can include sending or issuing a request for therapy to a third party such as a care provider, a clinician, an emergency services responder, or the like.

In some embodiments, the therapy can include the administration of at least one of a clot dissolving agent or an anticoagulant. Exemplary clot dissolving agents can include streptokinase, tissue plasminogen activator and the like. Exemplary anticoagulants can include aspirin, clopidogrel, and the like.

In some embodiments initiating the administration of a therapy can include issuing a verbal, visual, or tactile instruction to the wearer to take a medication. In some embodiments the system can confirm that the wearer has taken a medication using methods such as those taught in Ser. No. 16/802,113 "SYSTEM AND METHOD FOR MANAGING PHARMACOLOGICAL THERAPEUTICS INCLUDING A HEALTH MONITORING DEVICE". In some embodiments, the system can send an alert or notification to a third party to inform them that the wearer has taken/not taken a medication in following the instruction.

Figure 2:
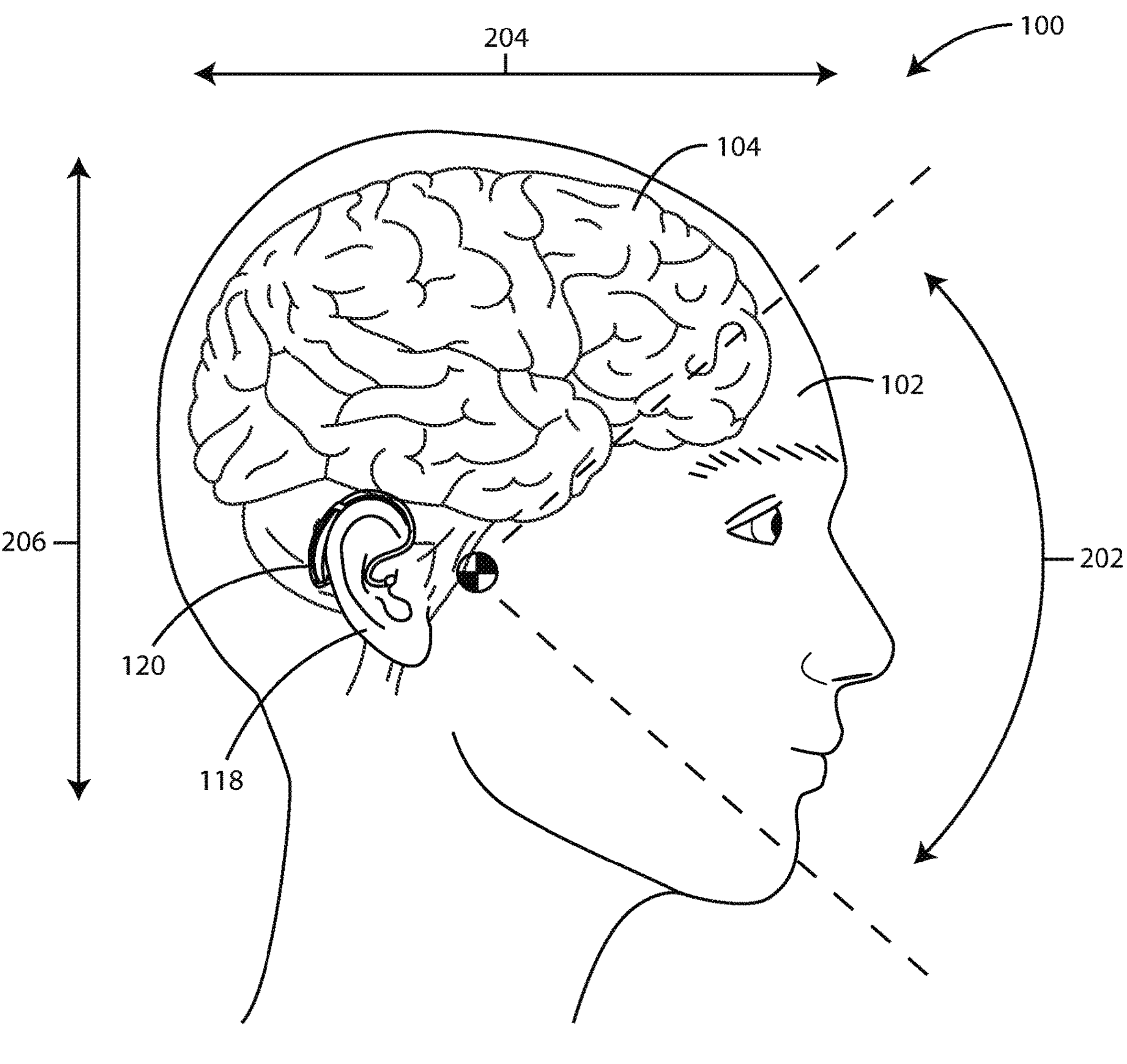
FIG. 2 is a schematic view of an ear-wearable device and wearer in accordance with various embodiments herein.
Figure 3:
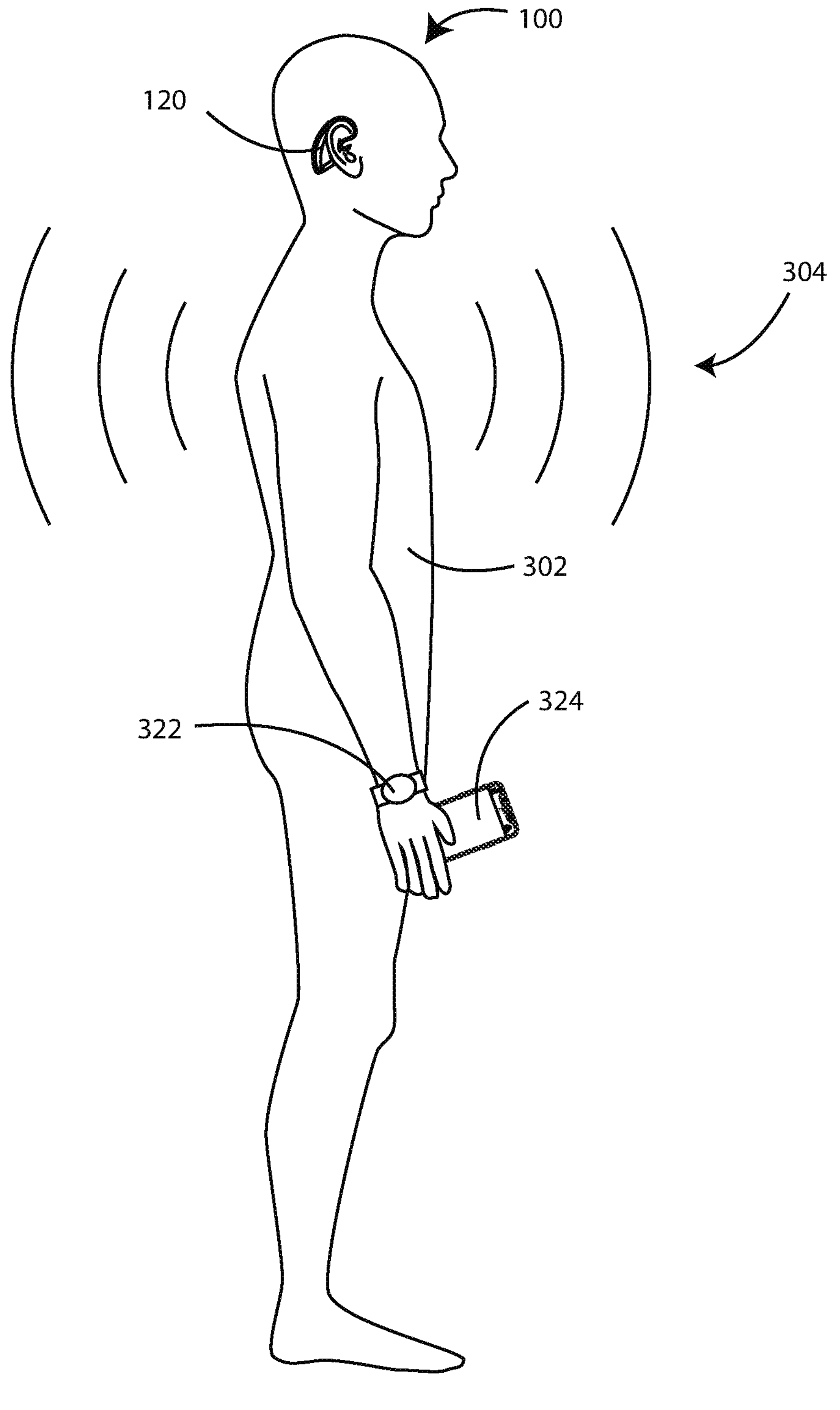
FIG. 3 is a schematic view of an ear-wearable device and wearer in accordance with various embodiments herein.

Referring now to FIG. 2, a schematic view is shown of an ear-wearable device 120 and device wearer 100. It will be appreciated that many different aspects of the device wearer 100 can be tracked with devices and systems herein. For example, in some embodiments the ear-wearable device 120 can include a motion sensor (described in greater detail below) and can sense movement of the device wearer 100. For example, with respect to both the head 102 of the device wearer 100 and other parts of their body, the system or device can sense rotational movement 202 (within multiple planes), front to back movement 204, up and down movement 206, pitch, roll, yaw, twisting motions, and the like. Referring now to FIG. 3, a schematic view of an ear-wearable device 120 and device wearer 100 is shown along with the body 302 of the device wearer 100. Other types of movement that can be sensed include body sway 304 (and in some scenarios can also include head sway). In some embodiments, such movements can be given an activity classification by the system.

As referenced above, many different patterns can be detected by the ear-wearable device and/or the ear-wearable device system in order to indicate the presence of a neurological injury. For example, in some embodiments, the ear-wearable device 120 can detect a pattern that is indicative of motor impairment. In various embodiments, the ear-wearable device 120 can detect a pattern is indicative of one or more of gait ataxia, difficulty standing or walking, or a sudden decrease in motor coordination. In various embodiments, the ear-wearable device 120 can detect a pattern is indicative of onset of dizziness or imbalance. In various embodiments, the ear-wearable device 120 wherein the ear-wearable device 120 is configured to detect a non-volitional body movement.

In some embodiments, patterns herein can relate to the individual's gait and which can be detected with a motion sensor herein including, for example, gait speed, step distance, bilateral step comparison, footfall magnitude, and the like.

In some embodiments, systems herein can include and/or receive inputs from or send outputs to other types of devices other than one or more ear-wearable devices. For example, in some embodiments the ear-wearable device can include or can receive inputs from a cardiac sensor. In such a case, a pattern herein can include a cardiac pattern such as atrial fibrillation. In some embodiments, a pattern herein can include a cardiac pattern such as beat variability.

FIG. 3 also shows a wearable device 322, which could be a smartwatch, a cardiac sensor/monitor, an oxygen sensor, or the like. FIG. 3 also shows an accessory device 324, which could be a smartphone, a tablet device, a general computing device, or the like. In some embodiments, the wearable device 322 and the accessory device 324 can both be part of the ear-wearable device system. In some embodiments, the wearable device 322 and the accessory device 324 can include sensors, such as any of the sensors described herein below. In some embodiments, they can send data to the ear-wearable device. In some embodiments, they can receive data from the ear-wearable device. In some embodiments, data obtained from one or more of the ear-wearable device 120, wearable device 322, and accessory device 324 can be used to assist in detecting indicators of possible ipsilesional limb ataxia.

In some cases, the system can include a motion sensor to pick up essential tremors (unintentional, somewhat rhythmic, muscle movement involving to-and-fro movements or oscillations of one or more parts of the body) of the wearer. By way of example, some individual suffering from a stroke suffer uncontrollable shaking that can be identified within the signals of various sensors herein including motion sensors.

In some embodiments, the system can detect dysphagia (swallowing difficulty), swallowing apraxia, buccofacial apraxia, and/or aspiration. Dysphagia, swallowing apraxia, buccofacial apraxia, and/or aspiration can be an indication of ischemic strokes or TIAs. The devices or system herein can detect dysphagia, swallowing apraxia, buccofacial apraxia, and/or aspiration using data from various sensors. By way of example, dysphagia, swallowing apraxia, buccofacial apraxia, and/or aspiration can be detected by detecting a signature or pattern in microphone data and/or motion sensor data. In some embodiments, detection of a signature or pattern of dysphagia, swallowing apraxia, buccofacial apraxia, and/or aspiration can be used herein as indicative of a neurological injury of the device wearer.

Figure 4:
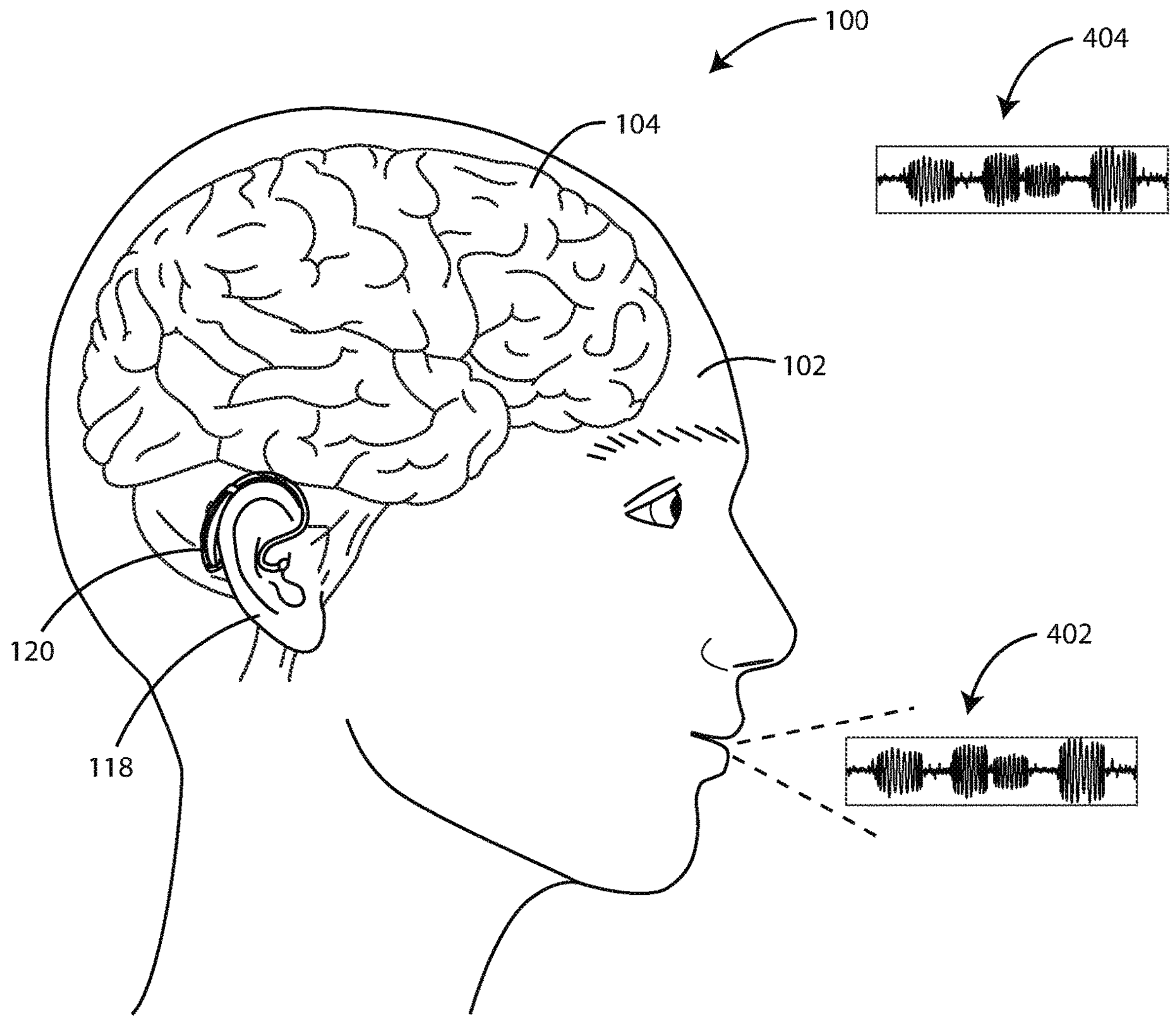
FIG. 4 is a schematic view of an ear-wearable device and wearer in accordance with various embodiments herein.

Referring now to FIG. 4, a schematic view of an ear-wearable device 120 and device wearer 100 is shown in accordance with various embodiments herein. In this case, various speech or noise within the environment of the device wearer 100 can be detected. For example, the ear-wearable device 120 can detect speech such as device wearer speech 402 as well as third party speech 404 or ambient noise.

It can be appreciated that while the ear-wearable device 120 should respond to patterns indicative of neurological injury of the device wearer 100, that it should typically not take the same actions when such patterns are only detected in that of a third party. As such, in various embodiments herein, the device or system can distinguish between speech or sounds associated with the device wearer 100 from speech or sounds associated with a third party. Processing to distinguish between the two can be executed by any devices of the system individually or by a combination of devices of the system. In some embodiments, data used for distinguishing can be exported from an ear-wearable device or devices to one or more separate devices for processing.

Distinguishing between speech or sounds associated with the device wearer 100 and speech or sounds associated with a third party can be performed in various ways. In some embodiments, this can be performed through signal analysis of the signals generated from the microphone(s). For example, in some embodiments, this can be done by filtering out frequencies of sound that are not associated with speech of the device-wearer. In some embodiments, such as where there are two or more microphones (on the same ear-wearable device or on different ear-wearable devices) this can be done through spatial localization of the origin of the speech or other sounds and filtering out, spectrally subtracting, or otherwise discarding sounds that do not have an origin within the device wearer 100. In some embodiments, such as where there are two or more ear-worn devices, own-voice detection can be performed and/or enhanced through correlation or matching of intensity levels and or timing.

In some cases, the system can include a bone conduction microphone in order to preferentially pickup the voice of the device wearer. In some cases, the system can include a directional microphone that is configured to preferentially pickup the voice of the device wearer. In some cases the system can include an intracanal microphone (a microphone configured to be disposed within the ear-canal of the device wearer) to preferentially pickup the voice of the device wearer. In some cases, the system can include a motion sensor (e.g., an accelerometer configured to be on or about the head of the wearer) to preferentially pick up skull vibrations associated with the vocal productions of the device wearer.

In some cases, an adaptive filtering approach can be used. By way of example, a desired signal for an adaptive filter can be taken from a first microphone and the input signal to the adaptive filter is taken from the second microphone. If the hearing aid wearer is talking, the adaptive filter models the relative transfer function between the microphones. Own-voice detection can be performed by comparing the power of an error signal produced by the adaptive filter to the power of the signal from the standard microphone and/or looking at the peak strength in the impulse response of the filter. The amplitude of the impulse response should be in a certain range in order to be valid for the own voice. If the user's own voice is present, the power of the error signal will be much less than the power of the signal from the standard microphone, and the impulse response has a strong peak with an amplitude above a threshold. In the presence of the user's own voice, the largest coefficient of the adaptive filter is expected to be within a particular range. Sound from other noise sources results in a smaller difference between the power of the error signal and the power of the signal from the standard microphone, and a small impulse response of the filter with no distinctive peak. Further aspects of this approach are described in U.S. Pat. No. 9,219,964, the content of which is herein incorporated by reference.

In another approach, system uses a set of signals from a number of microphones. For example, a first microphone can produce a first output signal A from a filter and a second microphone can produce a second output signal B from a filter. The apparatus includes a first directional filter adapted to receive the first output signal A and produce a first directional output signal. A digital signal processor is adapted to receive signals representative of the sounds from the user's mouth from at least one or more of the first and second microphones and to detect at least an average fundamental frequency of voice (pitch output) $F_0$. A voice detection circuit is adapted to receive the second output signal B and the pitch output $F_0$ and to produce an own voice detection trigger T. The apparatus further includes a mismatch filter adapted to receive and process the second output signal B, the own voice detection trigger T, and an error signal E, where the error signal E is a difference between the first output signal A and an output O of the mismatch filter. A second directional filter is adapted to receive the matched output O and produce a second directional output signal. A first summing circuit is adapted to receive the first directional output signal and the second directional output signal and to provide a summed directional output signal (D). In use, at least the first microphone and the second microphone are in relatively constant spatial position with respect to the user's mouth, according to various embodiments. Further aspects of this approach are described in U.S. Pat. No. 9,210,518, the content of which is herein incorporated by reference.

In various embodiments, the ear-wearable device 120 can detect a pattern based on the content of the ear-wearable device 120 wearer's speech utterances. In some cases, the content can include the words that are spoken by the device wearer. In some cases, the content can include the sounds (i.e., phonemes) or sound patterns other than words that are uttered by the device wearer. In some cases, the content can include both the words and other sounds or sound patterns.

Signals reflecting the ear-wearable device wearer's speech utterances can be transcribed into words or phonemes (i.e., speech recognition) in various ways. In some embodiments, a speech-to-text module can be included within the system herein or can be accessed as part of a remote system such as an API. For example, one such speech-to-text API is the Google Cloud Speech-to-Text API, wherein files/data representing speech can be submitted and text can be retrieved. Another is the speech service API from Microsoft Azure Cognitive Speech Services.

In some embodiments, the system can evaluate the number or classification of words or phonemes reflecting confusion as uttered by the ear-wearable device wearer can be tracked. Words of confusion can include "what?" "who?", "why?", "when?", "where?", "uh?", as well as others. In some embodiments, a value reflecting the number of words of confusion uttered per unit time (such as per minute, etc.) can be calculated. If this value changes substantially for an individual over a baseline value (such as by greater then 5, 10, 15, 20, 30, 50, 75, 100, 200 percent or more, or an amount falling within a range between any of the foregoing), then that can be taken as a pattern indicative of a neurological injury. In other embodiments, if such values cross threshold amounts, then that can be taken as a pattern indicative of a neurological injury.

In some embodiments, the system can use the transcription data (e.g., speech-to-text output data) associated with the device wearer's speech in order to verify whether the device wearer is answering questions correctly. For example, the system could provide a prompt, such as "what day is it?" and then wait for an answer from the device wearer. A series of similar questions could be asked and then the system could determine a score based on the number of correct answers. This could be done periodically over time. If this value is substantially reduced for an individual over a baseline value or if the score crosses a threshold amount, then that can be taken as a pattern indicative of a neurological injury.

In some embodiments, the system can present images of objects on a display screen and ask the user to identify the objects and the results can be scored. In some embodiments, the system can measure the amount of time required for the device wearer to answer an open-ended question such as describing their environment. In some embodiments, the system can administer a memory test such as providing information for the device wearer to remember and then asking them to recall the provided information. In some embodiments, the system can ask questions such as "tell me words that begin with the letter 'E'" and then score the answers, such as by counting the number of words generated by the device wearer that correctly begin with the letter "E". In some embodiments, the system could ask a question reflecting common knowledge such as "tell me the ingredients you might put on a pizza" and then score the results, such as by the total number of items stated by the device wearer. Any of these queries (or others) can be repeated periodically. If the resulting score or value changes substantially over a baseline value of if the score crosses a threshold amount, then that can be taken as a pattern indicative of a neurological injury. In some embodiments herein, queries can be generated and/or delivered by a component of the ear-wearable device system. However, in some embodiments, a third party may be generating and/or delivering the queries and a component of the ear-wearable device system can identify that a query is being delivered and monitor for a response.

It will be appreciated that speech patterns herein can include various features. In some embodiments, the speech pattern can include long delays. For example, the system can track the amount of time between words, between spoken sentences, and or the amount of time between a query and a response. In some cases, an average delay can be calculated. In some embodiments, a time ratio of delay to spoken word content time can be calculated for a given time period (e.g., total delay time per minute/total spoken word content time per minute). If such delays (in the absolute, as an average or other statistical measure, as a ratio, etc.) increase significantly over a baseline value (such as by greater then 5, 10, 15, 20, 30, 50, 75, 100, 200 percent or more, or an amount falling within a range between any of the foregoing), then that can be taken as a pattern indicative of a neurological injury. In other embodiments, if such values cross threshold amounts, then that can be taken as a pattern indicative of a neurological injury. In some embodiments, the amount of time that a particular speech phoneme is sustained may be atypically long or short.

In various embodiments, the speech pattern can include the clarity, breathiness, pitch change, vowel instability, and/or roughness of the ear-wearable device wearer's speech. In various embodiments, the speech pattern can include slurred utterances. In various embodiments, the speech pattern can include strained utterances. In various embodiments, the speech pattern can include quiet utterances. In various embodiments, the speech pattern can include raspy utterances. In various embodiments, the speech pattern can include changed pronunciation of words.

In some embodiments, speech patterns herein indicative of a neurological injury can include changes in speech complexity (e.g., semantic complexity, grammatical incompleteness, etc.) or fluency (e.g., atypical pause patterns) may be a signs of aphasia, dysarthria, dyspraxia or other speech-language processes associated with a stroke.

In some embodiments, the speech patterns (or other patterns described herein) can be used to determine the site of lesion/type of stroke that an individual may be experiencing or have experienced previously. For example, Wernicke's Aphasia is characterized by receptive language comprehension difficulties. In this example, the system can utilize content analyses to determine that an individual is not understanding what is being communicated to them by others, or that the individual is generating utterances that are nonsensical (e.g., the individual may string together a series of meaningless words that sound like a typical sentence but carries no little linguistic meaning to others), or that the individual is simply unable to complete or attempt the tests as directed. In another example, Broca's Aphasia is characterized by expressive language difficulties. In this example, the system can utilize the speech content to determine that the individual is not properly adhering to typical language conventions (e.g., the individual may utter some words that convey meaning but omit grammatical words like "is" or "the"; thereby making the utterance difficult for others to understand).

Figure 5:
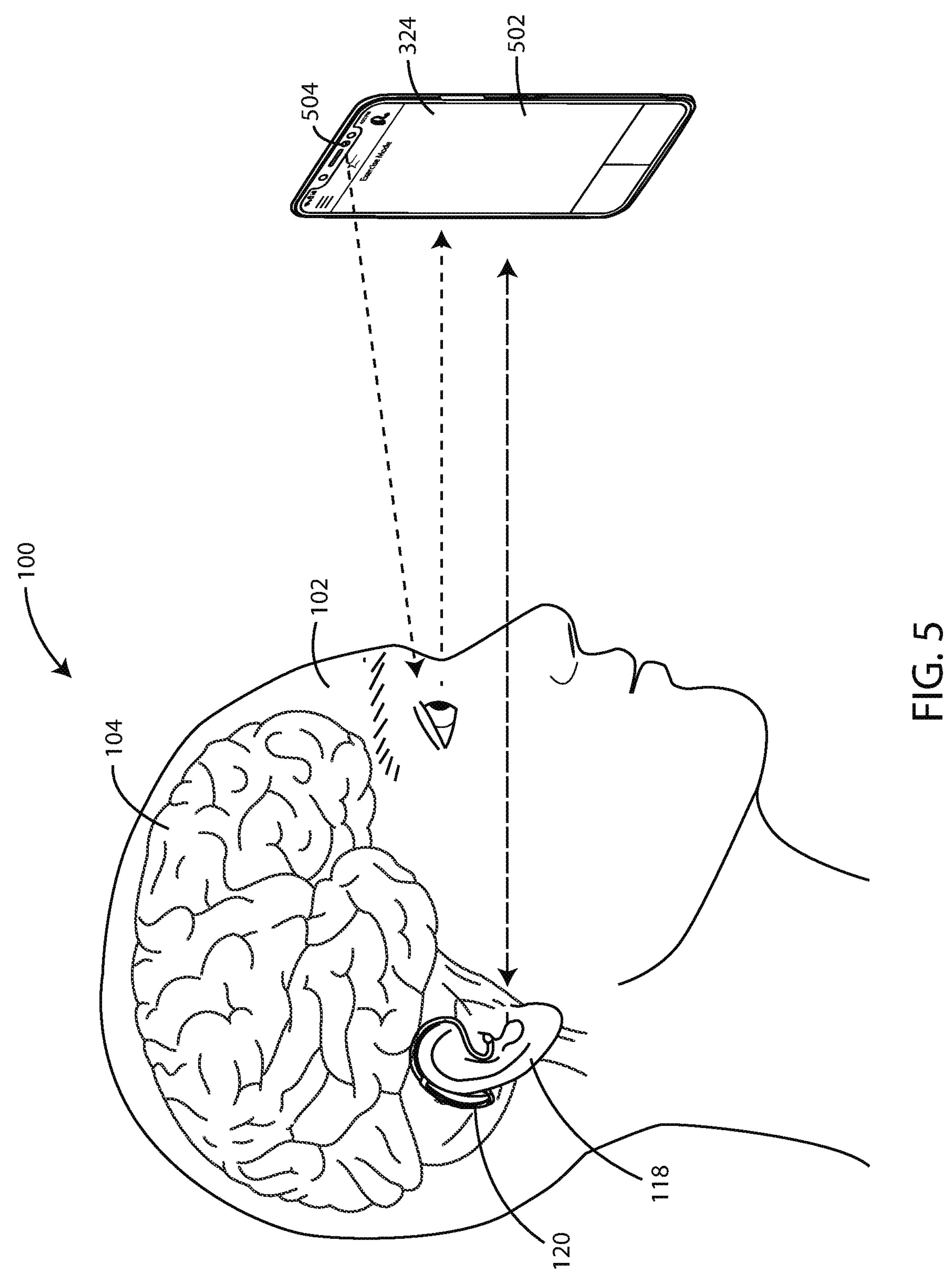
FIG. 5 is a schematic view of an ear-wearable device and wearer in accordance with various embodiments herein.

Referring now to FIG. 5, a schematic view of an ear-wearable device 120 and device wearer 100 is shown in accordance with various embodiments herein. The head 102 of the device wearer 100 is facing towards an accessory device 324. In specific, the device wearer 100 is looking at the accessory device 324. In this view, the accessory device 324 includes a display screen 502 and a camera 504.

The camera 504 of the accessory device 324 can be focused on the device wearer 100 and can detect various visual aspects/features of the device wearer 100. To facilitate this, in some embodiments the ear-wearable device 120 is configured to prompt the device wearer 100 to look at the accessory device 324 (equipped with a camera 504) if a pattern indicative of an occurrence of an anoxic or hypoxic neurological injury is detected.

Many different visual aspects/features are contemplated herein. In various embodiments, the ear-wearable device 120 can detect non-volitional eye movement by virtue of the camera 504 capturing images of the device wearer 100. In some embodiments, the ear-wearable device 120 can be configured to detect eye dilation. In various embodiments, the ear-wearable device 120 can be configured to detect facial paralysis, face droop or actions that may be consistent with drooling such as characteristic head movements associated with wiping of the device wearer's face.

Figure 6:
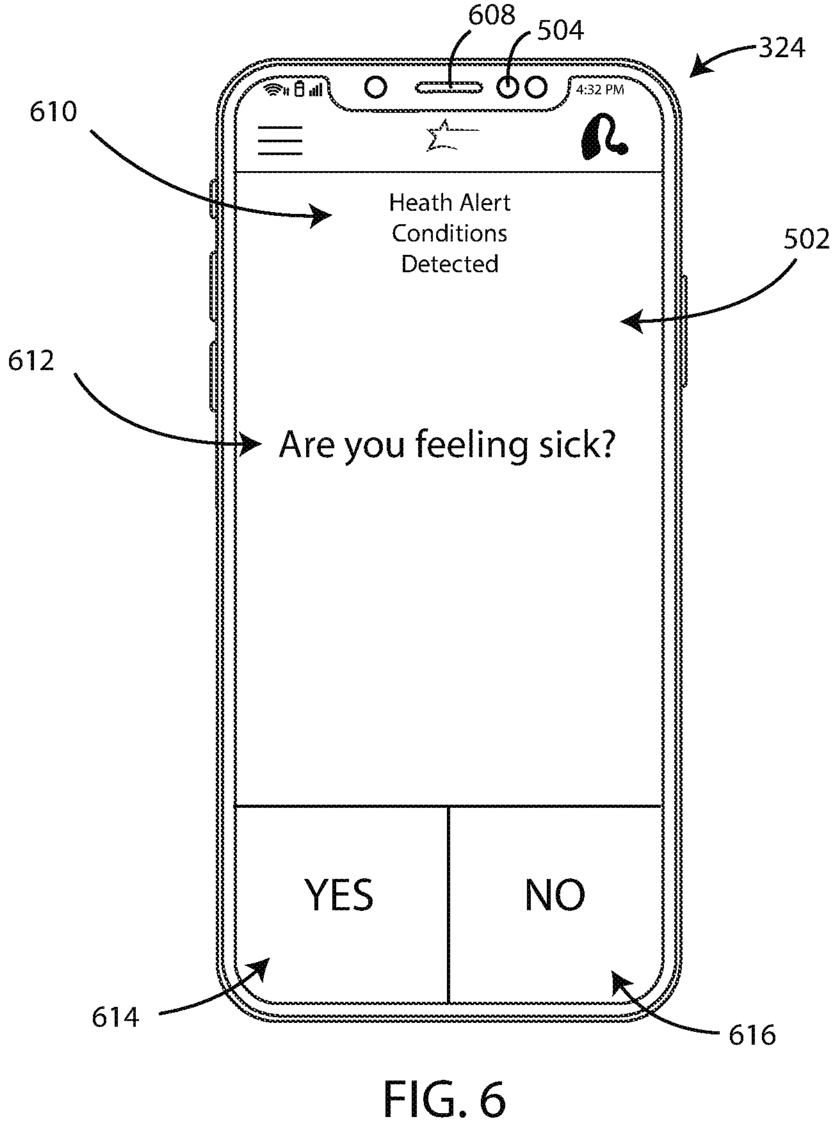
FIG. 6 is a schematic view of an accessory device in accordance with various embodiments herein.

In various embodiments, the ear-wearable device 120 can be configured to query the device wearer 100. Referring now to FIG. 6, a schematic view of an accessory device 324 is shown in accordance with various embodiments herein. The accessory device can include display screen 502, camera 504, speaker 608, notification 610, query 612, first user input button 614, and second user input button 616. In this example, the ear-wearable device 120 can be configured to query the device wearer 100 if a pattern indicative of an occurrence of an anoxic or hypoxic neurological injury can be detected. For example, in some cases the query could be as simple as "Are you feeling sick?" as shown in FIG. 6. The individual can then respond by interfacing with one of the user input buttons or simply speaking their answer. In some embodiments, a response indicating that the individual is not feeling well, is feeling numb, is feeling dizzy, is experiencing changes in hearing or perception of tinnitus, is feeling pain, or is experiencing another symptom of a stroke can be taken as part of an indication or pattern that the individual may be suffering from a neurological injury.

It will be appreciated that queries can take on many different forms. In some embodiments, the query can be visual, aural, tactile or the like. In some embodiments, the query can request device wearer feedback or input (such as could be provided through a button press, an oral response, a movement, etc.). In some embodiments, the query can take the form of a question regarding how the device wearer 100 is feeling or what they are experiencing. In some embodiments, the query can relate to whether they are experiencing weakness. In some embodiments, the query can take the form of a question which requires a degree of cognition in order to answer, such as a math question, a verbal question, a question about their person information (such as one for which the answer is already known by the system), or the like. In some cases, the query can target a response which tests a specific function/area of the brain (e.g., a specific language ability like differentiating phonological or semantic differences between test stimuli). In some cases, there can be a single query. In some cases, there can be multiple queries.

In some embodiments, the ear-wearable device 120 can be configured to evaluate a nature or quality of a response from the device wearer 100 in response to the query. For example, in the context of a question, the system can evaluate whether the answer to the question suggests they are feeling ill or experiencing a symptom of a neurological injury. As another example, the system can evaluate whether the answer to a question is correct or not. As another example, the system can evaluate the amount of time taken for the device wearer to answer a question. Of course, in some cases a device wearer may simply not respond to a query. In some embodiments, the system can interpret the lack of a response as being indicative of one or more of an occurrence, prodrome or sequelae of an anoxic or hypoxic neurological injury. However, in other embodiments, the system can be configured so as to not interpret the lack of a response that way. In some embodiments, the system can be configured to allow the user to cease or skip further testing.

Figure 7:
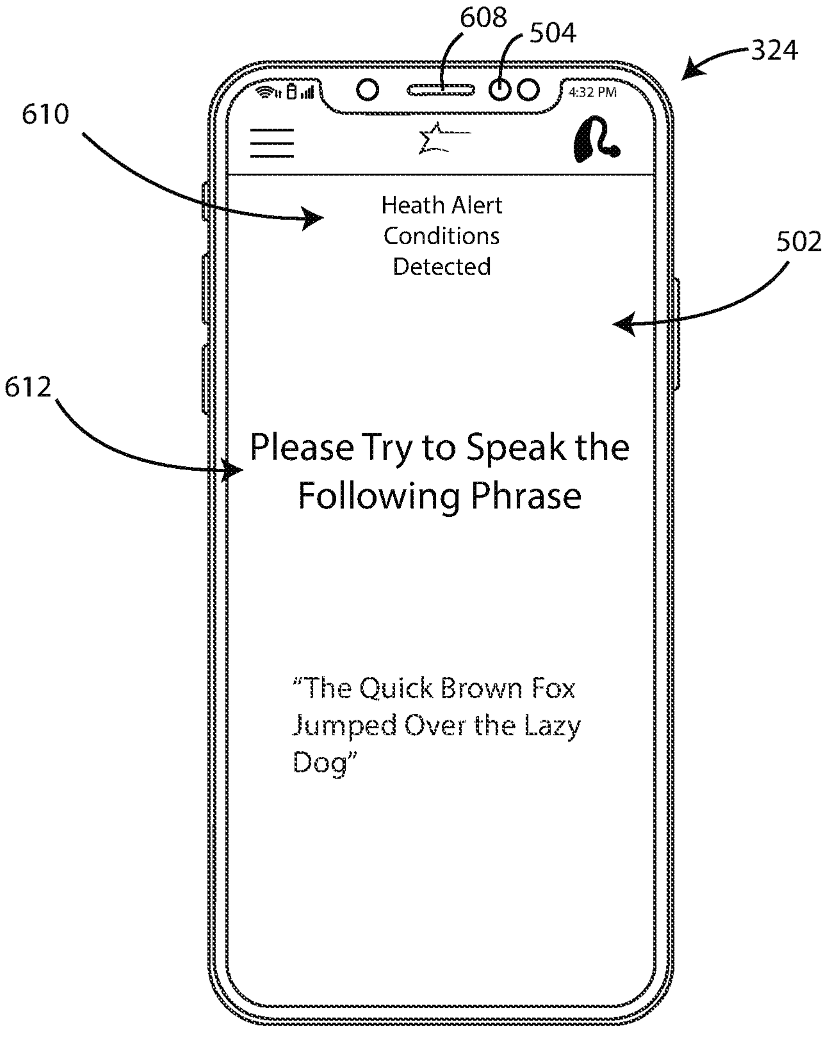
FIG. 7 is a schematic view of an accessory device in accordance with various embodiments herein.

In some embodiments, a query can specifically take the form of a request or prompt for the device wearer 100 to do or say something. Referring now to FIG. 7, a schematic view of an accessory device 324 is shown in accordance with various embodiments herein. In various embodiments, the ear-wearable device 120 is configured to prompt the device wearer 100 if a pattern indicative of one or more of an occurrence, prodrome or sequelae of an anoxic or hypoxic neurological injury is detected. In some embodiments, the ear-wearable device 120 wherein the query comprises a prompt to move in a certain way (e.g., "please lift your arm", "touch your right ear", etc.). In some embodiments, the ear-wearable device 120 wherein the query comprises a prompt to execute a specific movement protocol.

Ear-wearable devices herein, including hearing aids and hearables (e.g., wearable earphones), can include an enclosure, such as a housing or shell, within which internal components are disposed. Components of an ear-wearable device herein can include a control circuit, digital signal processor (DSP), memory (such as non-volatile memory), power management circuitry, a data communications bus, one or more communication devices (e.g., a radio, a near-field magnetic induction device), one or more antennas, one or more microphones, a receiver/speaker, a telecoil, and various sensors as described in greater detail below. More advanced ear-wearable devices can incorporate a long-range communication device, such as a BLUETOOTH® transceiver or other type of radio frequency (RF) transceiver.

Figure 8:
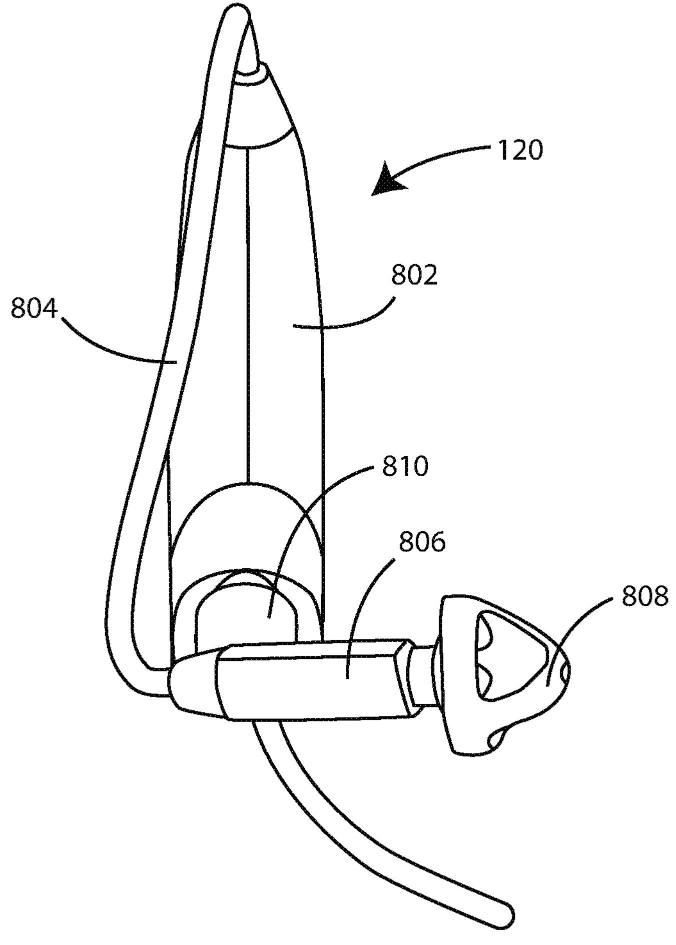
FIG. 8 is a schematic view of an ear-wearable device in accordance with various embodiments herein.

Referring now to FIG. 8, a schematic view of an ear-wearable device 120 is shown in accordance with various embodiments herein. The ear-wearable device 120 can include a hearing device housing 802. The hearing device housing 802 can define a battery compartment 810 into which a battery can be disposed to provide power to the device. The ear-wearable device 120 can also include a receiver 806 adjacent to an earbud 808. The receiver 806 an include a component that converts electrical impulses into sound, such as an electroacoustic transducer, speaker, or loud speaker. Such components can be used to generate an audible stimulus in various embodiments herein. A cable 804 or connecting wire can include one or more electrical conductors and provide electrical communication between components inside of the hearing device housing 802 and components inside of the receiver 806.

The ear-wearable device 120 shown in FIG. 8 is a receiver-in-canal type device and thus the receiver is designed to be placed within the ear canal. However, it will be appreciated that many different form factors for ear-wearable devices are contemplated herein. As such, ear-wearable devices herein can include, but are not limited to, behind-the-ear (BTE), in-the ear (ITE), in-the-canal (ITC), invisible-in-canal (IIC), receiver-in-canal (RIC), receiver in-the-ear (RITE), completely-in-the-canal (CIC) type hearing assistance devices, a personal sound amplifier, a cochlear implant, a bone-anchored or otherwise osseo-integrated hearing device, or the like.

Ear-wearable devices of the present disclosure can incorporate an antenna arrangement coupled to a high-frequency radio, such as a 2.4 GHz radio. The radio can conform to an IEEE 802.11 (e.g., WIFI®) or BLUETOOTH® (e.g., BLE, BLUETOOTH® 4.2 or 5.0) specification, for example. It is understood that ear-wearable devices of the present disclosure can employ other radios, such as a 900 MHz radio. Ear-wearable devices of the present disclosure can be configured to receive streaming audio (e.g., digital audio data or files) from an electronic or digital source. Representative electronic/digital sources (also referred to herein as accessory devices) include an assistive listening system, a TV streamer, a remote microphone device, a radio, a smartphone, a cell phone/entertainment device (CPED), a programming device, or other electronic device that serves as a source of digital audio data or files.

Figure 9:
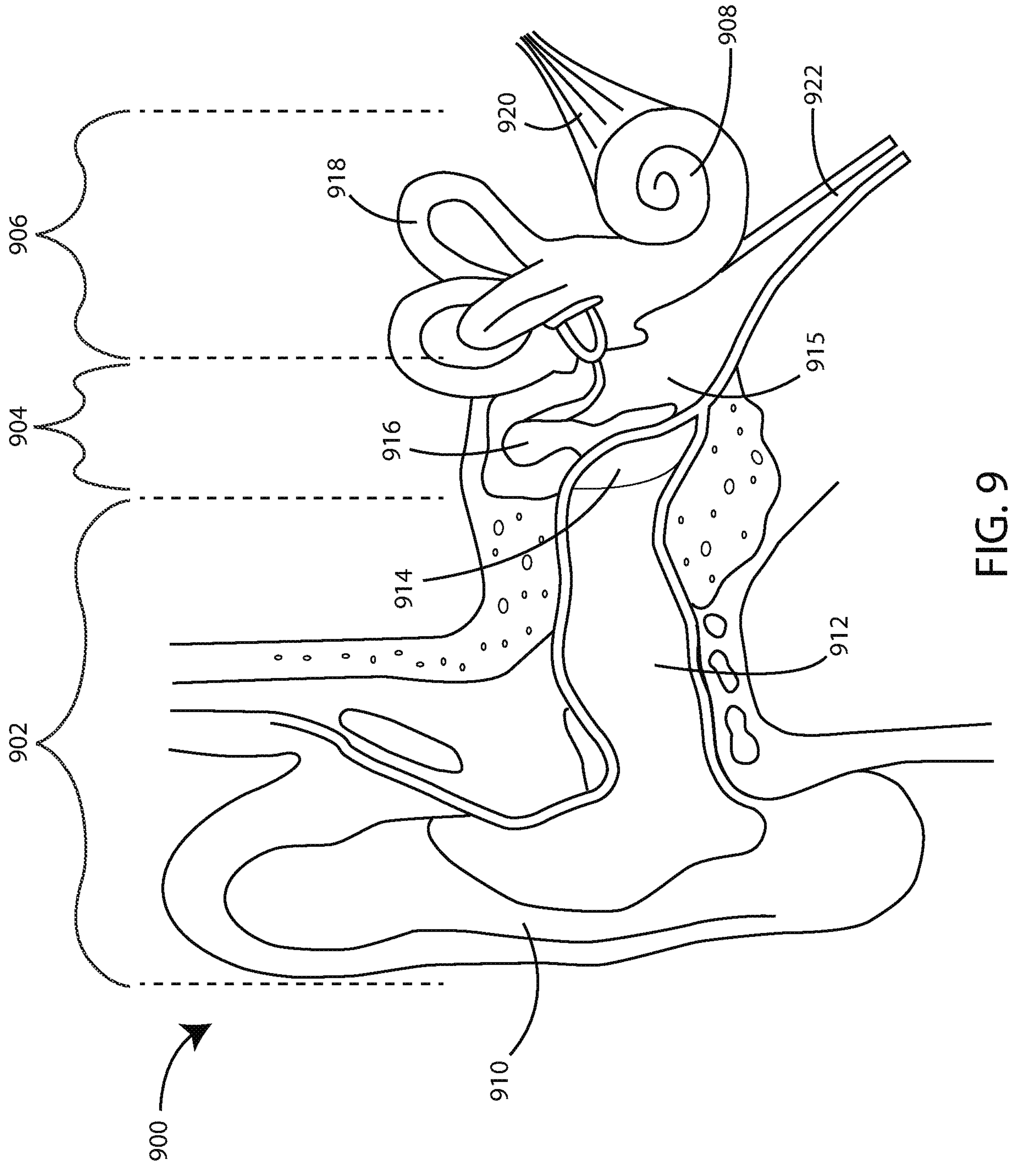
FIG. 9 is a schematic view of the anatomy of the ear in accordance with various embodiments herein.

Referring now to FIG. 9, a partial cross-sectional view of ear anatomy is shown. The three parts of the ear anatomy are the outer ear 902, the middle ear 904 and the inner ear 906. The outer ear 902 includes the pinna 910, ear canal 912, and the tympanic membrane 914 (or eardrum). The middle ear 904 includes the tympanic cavity 915, auditory bones 916 (malleus, incus, stapes), and a portion of the facial nerve. The pharyngotympanic tube 922 is in fluid communication with the eustachian tube and helps to control pressure within the middle ear generally making it equal with ambient air pressure. The inner ear 906 includes the cochlea 908 ('Cochlea' means 'snail' in Latin; the cochlea gets its name from its distinctive coiled up shape), and the semicircular canals 918, and the auditory nerve 920.

Sound waves enter the ear canal 912 and make the tympanic membrane 914 vibrate. This action moves the tiny chain of auditory bones 916 (ossicles—malleus, incus, stapes) in the middle ear 904. The last bone in this chain contacts the membrane window of the cochlea 908 and makes the fluid in the cochlea 908 move. The fluid movement then triggers a response in the auditory nerve 920.

Figure 10:
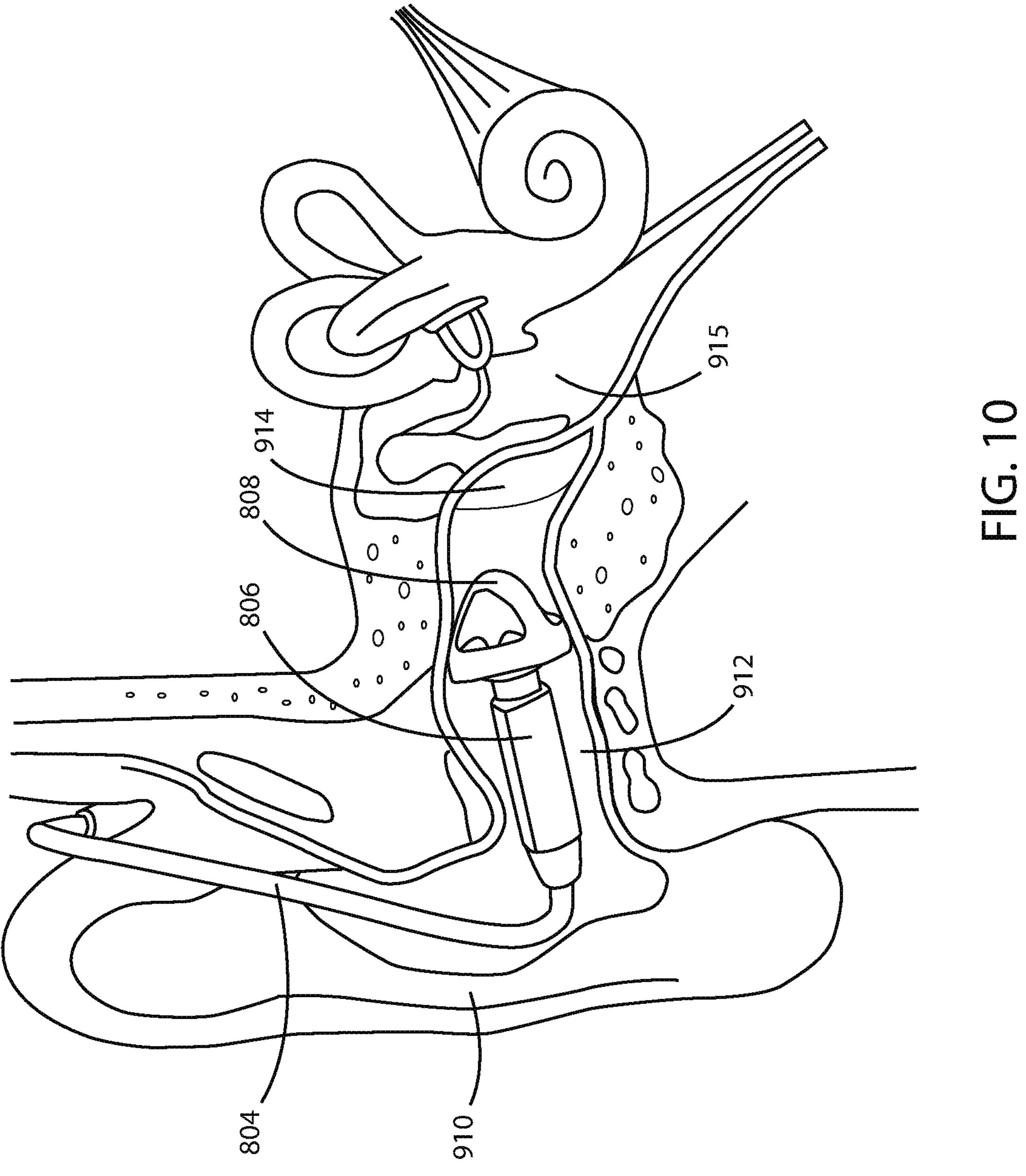
FIG. 10 is a schematic view of an ear-wearable device with the anatomy of the ear in accordance with various embodiments herein.

As mentioned above, the ear-wearable device 120 can be a receiver-in-canal type device and thus the receiver is designed to be placed within the ear canal. Referring now to FIG. 10, a schematic view is shown of an ear-wearable device disposed within the ear of a subject in accordance with various embodiments herein. In this view, the receiver 806 and the earbud 808 are both within the ear canal 912, but do not directly contact the tympanic membrane 914. The hearing device housing is mostly obscured in this view behind the pinna 910, but it can be seen that the cable 804 passes over the top of the pinna 910 and down to the entrance to the ear canal 912.

Figure 11:
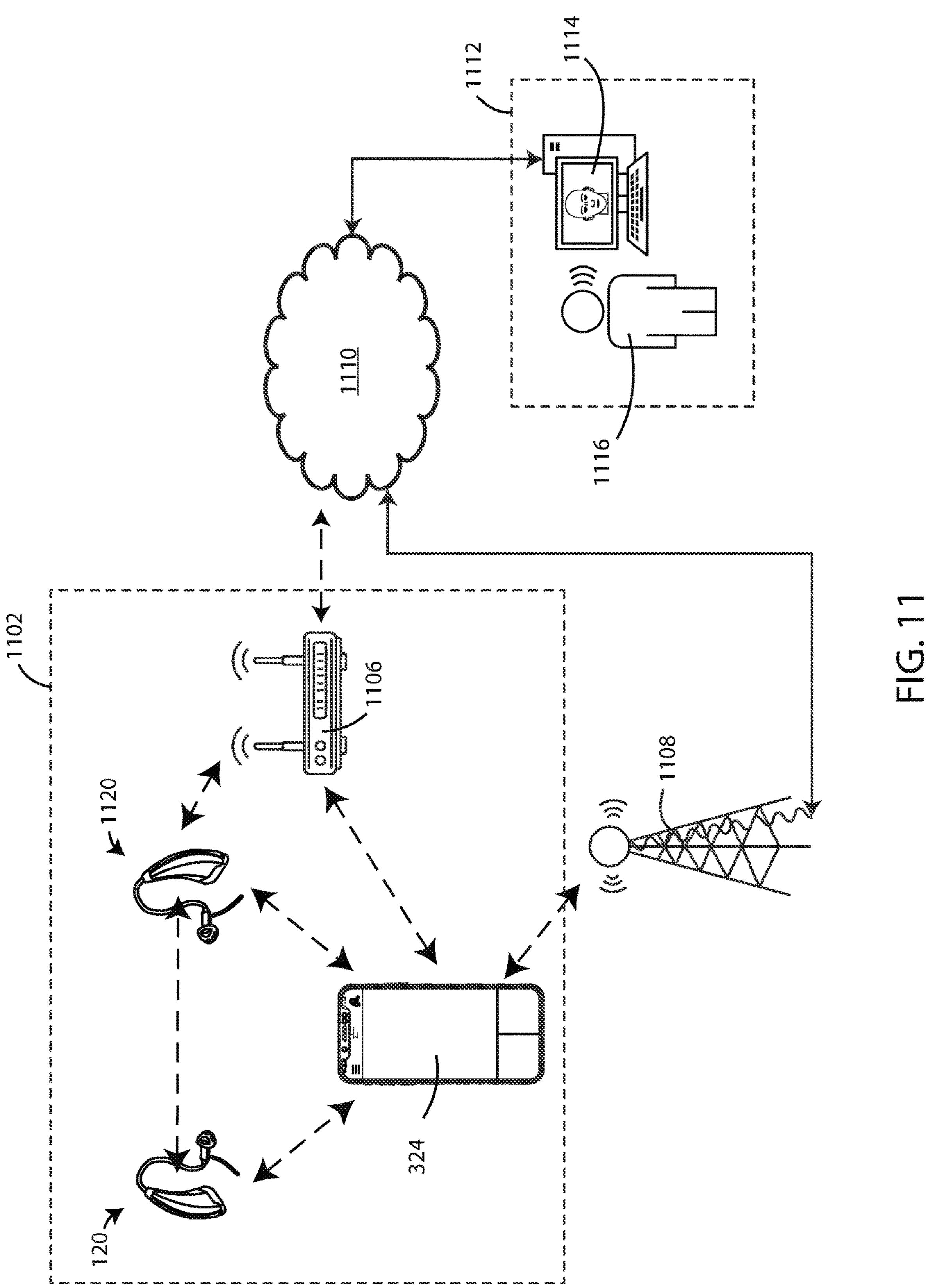
FIG. 11 is a schematic view of an ear-wearable device system in accordance with various embodiments herein.

Referring now to FIG. 11, a schematic view is shown of data and/or signal flow as part of a system in accordance with various embodiments herein. In a first location 1102, a device wearer (not shown) can have a first ear-wearable device 120 and a second ear-wearable device 1120. Each of the ear-wearable devices 120, 1120 can include sensor packages as described herein including, for example, an IMU. The ear-wearable devices 120, 1120 and sensors therein can be disposed on opposing lateral sides of the subject's head. In some embodiments, the ear-wearable devices 120, 1120 and sensors therein can be disposed in a fixed position relative to the subject's head. The ear-wearable devices 120, 1120 and sensors therein can be disposed within opposing ear canals of the subject. The ear-wearable devices 120, 1120 and sensors therein can be disposed on or in opposing ears of the subject. The ear-wearable devices 120, 1120 and sensors therein can be spaced apart from one another by a distance of at least 3, 4, 5, 6, 8, 10, 12, 14, or 16 centimeters and less than 40, 30, 28, 26, 24, 22, 20 or 18 centimeters, or by a distance falling within a range between any of the foregoing.

In various embodiments, data and/or signals can be exchanged directly between the first ear-wearable device

120 and the second ear-wearable device 1120. An accessory device 324 (which could be an external visual display device with a video display screen, such as a smart phone amongst other things) can also be disposed within the first location 1102. The accessory device 324 can exchange data and/or signals with one or both of the first ear-wearable device 120 and the second ear-wearable device 1120 and/or with an accessory to the ear-wearable devices (e.g., a remote microphone, a remote control, a phone streamer, etc.). The accessory device 324 can also exchange data across a data network to the cloud 1110, such as through a wireless signal connecting with a local gateway device, such as a network router 1106, mesh network, or through a wireless signal connecting with a cell tower 1108 or similar communications tower. In some embodiments, the external visual display device can also connect to a data network to provide communication to the cloud 1110 through a direct wired connection.

In some embodiments, a care provider 1116 (such as an audiologist, speech-language pathologist, physical therapist, occupational therapist, a physician or a different type of clinician, specialist, or care provider) can receive information from devices at the first location 1102 remotely at a second location 1112 through a data communication network such as that represented by the cloud 1110. The care provider 1116 can use a computing device 1114 to see and interact with the information received. The computing device 1114 could be a computer, a tablet device, a smartphone, or the like. The received information can include, but is not limited to, information regarding the subject's response time (reaction time and/or reflex time). In some embodiments, received information can be provided to the care provider 1116 in real time. In some embodiments, received information can be stored and provided to the care provider 1116 at a time point after response times are measured.

In some embodiments, the care provider 1116 (such as an audiologist, physical therapist, a physician or a different type of clinician, specialist, or care provider, or physical trainer) can send information remotely from the second location 1112 through a data communication network such as that represented by the cloud 1110 to devices at the first location 1102. For example, the care provider 1116 can enter information into the computing device 1114, can use a camera connected to the computing device 1114 and/or can speak into the external computing device. The sent information can include, but is not limited to, feedback information, guidance information, and the like. In some embodiments, feedback information from the care provider 1116 can be provided to the subject in real time.

As such, embodiments herein can include operations of sending data to a remote system user at a remote site, receiving feedback from the remote system user, and presenting the feedback to the subject. The operation of presenting the auditory feedback to the subject can be performed with the ear-wearable device (s). In various embodiments, the operation of presenting the auditory feedback to the subject can be performed with an ear-wearable device(s).

Ear-wearable devices of the present disclosure can incorporate an antenna arrangement coupled to a high-frequency radio, such as a 2.4 GHz radio. The radio can conform to an IEEE 802.11 (e.g., WIFI®) or BLUETOOTH® (e.g., BLE, BLUETOOTH® 4.2 or 5.0) specification, for example. It is understood that ear-wearable devices of the present disclosure can employ other radios, such as a 900 MHz radio or radios operating at other frequencies or frequency bands. Ear-wearable devices of the present disclosure can be configured to receive streaming audio (e.g., digital audio data or files) from an electronic or digital source. Representative electronic/digital sources (also referred to herein as accessory devices) include an assistive listening system, a TV streamer, a radio, a smartphone, a cell phone/entertainment device (CPED) or other electronic device that serves as a source of digital audio data or files. Systems herein can also include these types of accessory devices as well as other types of devices.

Figure 12:
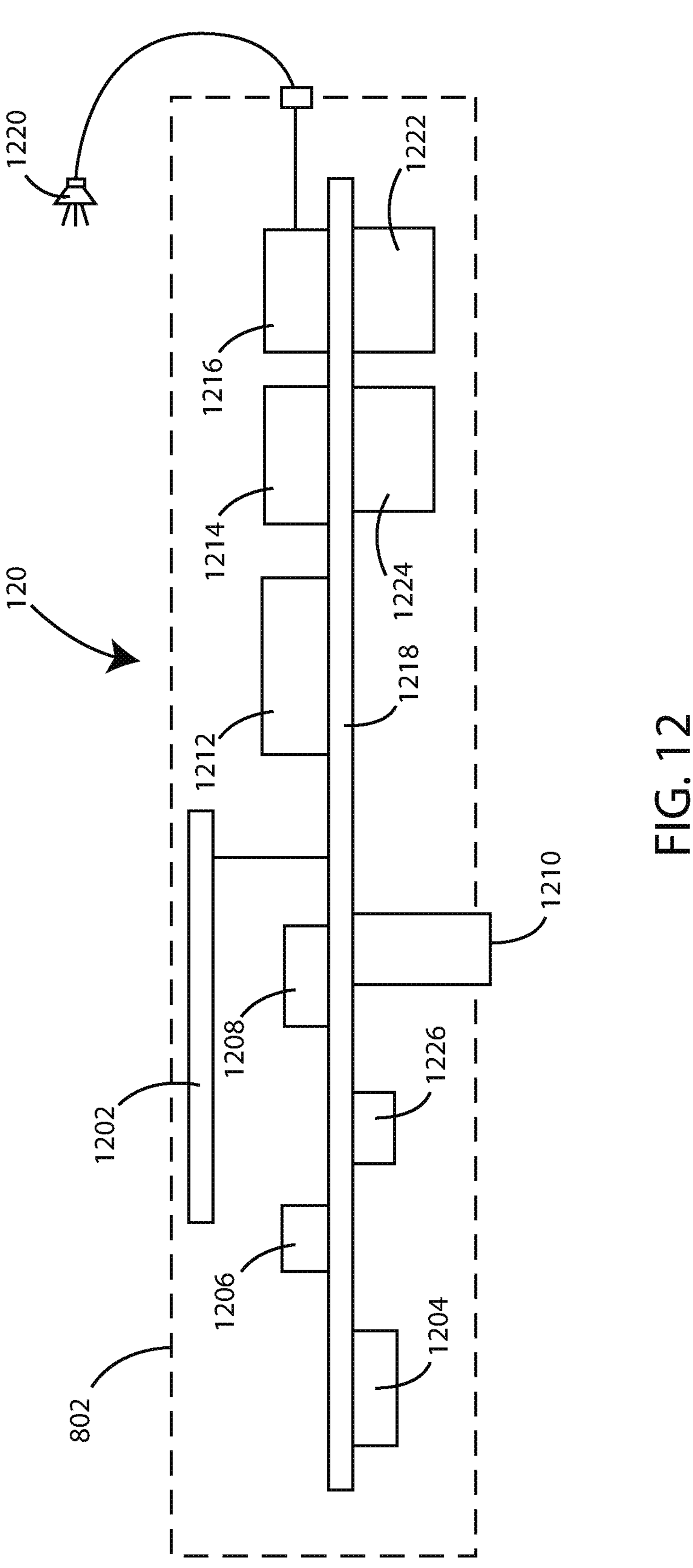
FIG. 12 is a schematic view of components of an ear-wearable device in accordance with various embodiments herein.

Referring now to FIG. 12, a schematic block diagram is shown with various components of an ear-wearable device in accordance with various embodiments. The block diagram of FIG. 12 represents a generic ear-wearable device for purposes of illustration. The ear-wearable device 120 shown in FIG. 12 includes several components electrically connected to a flexible mother circuit 1218 (e.g., flexible mother board) which is disposed within housing 802. A power supply circuit 1204 can include a battery and can be electrically connected to the flexible mother circuit 1218 and provides power to the various components of the ear-wearable device 120. One or more microphones 1206 are electrically connected to the flexible mother circuit 1218, which provides electrical communication between the microphones 1206 and a digital signal processor (DSP) 1212. Among other components, the DSP 1212 incorporates or is coupled to audio signal processing circuitry configured to implement various functions described herein. A sensor package 1214 can be coupled to the DSP 1212 via the flexible mother circuit 1218. The sensor package 1214 can include one or more different specific types of sensors such as those described in greater detail below. One or more user switches 1210 (e.g., on/off, volume, mic directional settings) are electrically coupled to the DSP 1212 via the flexible mother circuit 1218. It will be appreciated that the user switches 1210 can extend outside of the housing 802.

An audio output device 1216 is electrically connected to the DSP 1212 via the flexible mother circuit 1218. In some embodiments, the audio output device 1216 comprises a speaker (coupled to an amplifier). In other embodiments, the audio output device 1216 comprises an amplifier coupled to an external receiver 1220 adapted for positioning within an ear of a wearer. The external receiver 1220 can include an electroacoustic transducer, speaker, or loud speaker. The ear-wearable device 120 may incorporate a communication device 1208 coupled to the flexible mother circuit 1218 and to an antenna 1202 directly or indirectly via the flexible mother circuit 1218. The communication device 1208 can be a BLUETOOTH® transceiver, such as a BLE (BLUETOOTH® low energy) transceiver or other transceiver(s) (e.g., an IEEE 802.11 compliant device). The communication device 1208 can be configured to communicate with one or more external devices, such as those discussed previously, in accordance with various embodiments. In various embodiments, the communication device 1208 can be configured to communicate with an external visual display device such as a smart phone, a video display screen, a tablet, a computer, or the like.

In various embodiments, the ear-wearable device 120 can also include a control circuit 1222 and a memory storage device 1224. The control circuit 1222 can be in electrical communication with other components of the device. In some embodiments, a clock circuit 1226 can be in electrical communication with the control circuit. The control circuit 1222 can execute various operations, such as those described herein. The control circuit 1222 can include various components including, but not limited to, a microprocessor, a microcontroller, an FPGA (field-programmable gate array) processing device, an ASIC (application specific integrated circuit), or the like. The memory storage device 1224 can include both volatile and non-volatile memory. The memory storage device 1224 can include ROM, RAM, flash memory, EEPROM, SSD devices, NAND chips, and the like. The memory storage device 1224 can be used to store data from sensors as described herein and/or processed data generated using data from sensors as described herein.

It will be appreciated that various of the components described in FIG. 12 can be associated with separate devices and/or accessory devices to the ear-wearable device. By way of example, microphones can be associated with separate devices and/or accessory devices. Similarly, audio output devices can be associated with separate devices and/or accessory devices to the ear-wearable device. Further accessory devices as discussed herein can include various of the components as described with respect to an ear-wearable device. For example, an accessory device can include a control circuit, a microphone, a motion sensor, and a power supply, amongst other things.

Pattern Identification

It will be appreciated that in various embodiments herein, a device or a system can be used to detect a pattern or patterns indicative of an occurrence of an anoxic or hypoxic neurological injury. Such patterns can be detected in various ways. Some techniques are described elsewhere herein, but some further examples will now be described.

As merely one example, one or more sensors can be operatively connected to a controller (such as the control circuit describe in FIG. 12) or another processing resource (such as a processor of another device or a processing resource in the cloud). The controller or other processing resource can be adapted to receive data representative of a characteristic of the subject from one or more of the sensors and/or determine statistics of the subject over a monitoring time period based upon the data received from the sensor. As used herein, the term "data" can include a single datum or a plurality of data values or statistics. The term "statistics" can include any appropriate mathematical calculation or metric relative to data interpretation, e.g., probability, confidence interval, distribution, range, or the like. Further, as used herein, the term "monitoring time period" means a period of time over which characteristics of the subject are measured and statistics are determined. The monitoring time period can be any suitable length of time, e.g., 1 millisecond, 1 second, 10 seconds, 30 seconds, 1 minute, 10 minutes, 30 minutes, 1 hour, etc., or a range of time between any of the foregoing time periods.

Any suitable technique or techniques can be utilized to determine statistics for the various data from the sensors, e.g., direct statistical analyses of time series data from the sensors, differential statistics, comparisons to baseline or statistical models of similar data, etc. Such techniques can be general or individual-specific and represent long-term or short-term behavior. These techniques could include standard pattern classification methods such as Gaussian mixture models, clustering as well as Bayesian approaches, neural network models and deep learning.

Further, in some embodiments, the controller can be adapted to compare data, data features, and/or statistics against various other patterns, which could be prerecorded patterns (baseline patterns) of the particular individual wearing an ear-wearable device herein, prerecorded patterns (group baseline patterns) of a group of individuals wearing ear-wearable devices herein, one or more predetermined patterns that serve as patterns indicative of indicative of an occurrence of an anoxic or hypoxic neurological injury (positive example patterns), one or more predetermined patterns that service as patterns indicative of the absense of an occurrence of an anoxic or hypoxic neurological injury (negative example patterns), or the like. As merely one scenario, if a pattern is detected in an individual that exhibits similarity crossing a threshold value to a positive example pattern or substantial similarity to that pattern, then that can be taken as an indication of an occurrence of an anoxic or hypoxic neurological injury.

Similarity and dissimilarity can be measured directly via standard statistical metrics such normalized Z-score, or similar multidimensional distance measures (e.g. Mahalanobis or Bhattacharyya distance metrics), or through similarities of modeled data and machine learning. These techniques can include standard pattern classification methods such as Gaussian mixture models, clustering as well as Bayesian approaches, neural network models, and deep learning.

As used herein the term "substantially similar" means that, upon comparison, the sensor data are congruent or have statistics fitting the same statistical model, each with an acceptable degree of confidence. The threshold for the acceptability of a confidence statistic may vary depending upon the subject, sensor, sensor arrangement, type of data, context, condition, etc.

The statistics associated with the health status of an individual (and, in particular, their status with respect to an anoxic or hypoxic neurological insult/injury), over the monitoring time period, can be determined by utilizing any suitable technique or techniques, e.g., standard pattern classification methods such as Gaussian mixture models, clustering, hidden Markov models, as well as Bayesian approaches, neural network models, and deep learning.

Methods

Many different methods are contemplated herein. Aspects of system/device operation described elsewhere herein can be performed as operations of one or more methods in accordance with various embodiments herein.

In some embodiments, a method of monitoring an ear-wearable device wearer for an occurrence of an anoxic or hypoxic neurological insult/injury is included. In some embodiments, a method herein can include monitoring signals from a microphone, a motion sensor, and/or other sensors to detect patterns indicative of an occurrence of an anoxic or hypoxic neurological injury.

In an embodiment, a method of monitoring an ear-wearable device wearer for an occurrence of an anoxic or hypoxic neurological injury is included, the method including gathering signals from a microphone, a motion sensor, or another sensor of an ear-wearable device and monitoring the signals to detect a pattern indicative of an occurrence of an anoxic or hypoxic neurological injury.

Various patterns indicative of an occurrence of an anoxic or hypoxic neurological injury can be detected. In an embodiment, the pattern can include the content of the ear-wearable device wearer's speech. In an embodiment, the pattern can include words indicating confusion. In an embodiment, the pattern can include speech patterns of the ear-wearable device wearer's speech. In an embodiment, the pattern can include long delays.

In an embodiment, the pattern comprising the clarity, breathiness, pitch change, vowel instability, and/or roughness of the ear-wearable device wearer's speech. In an embodiment, the pattern can include slurred words. In an embodiment, the pattern can include changed pronunciation. In an embodiment, the pattern can include slurred words.

In an embodiment of the method, the pattern is indicative of motor impairment. In an embodiment of the method, the pattern is indicative of a sudden decrease in coordination. In an embodiment of the method, the pattern is indicative of sudden dizziness.

In an embodiment, the method can further include querying the device wearer if a pattern indicative of an occurrence of an anoxic or hypoxic neurological injury is detected. In an embodiment, the method can further include prompting the device wearer to look at an accessory device equipped with a camera if a pattern indicative of an occurrence of an anoxic or hypoxic neurological injury is detected. In an embodiment, a detected pattern can include eye dilation. In an embodiment, the pattern can include non-volitional eye movement. In an embodiment, the pattern can include face droop.

In an embodiment of the method, the query comprises a prompt to execute a movement protocol.

In an embodiment, the method can further include identifying a cardiac pattern indicative of an occurrence of an anoxic or hypoxic neurological injury. In an embodiment, the cardiac pattern can include atrial fibrillation. In an embodiment, the cardiac pattern can include beat variability.

In an embodiment, the method can further include generating an alert if an occurrence of an anoxic or hypoxic neurological injury is detected. In an embodiment of the method, the alert is generated according to a tiered alert classification.

In an embodiment, the method can further include marking the time of first detection of a pattern indicative of an occurrence of an anoxic or hypoxic neurological injury and subsequently transmitting the same for receipt by a care provider.

In an embodiment, the method can further include detecting a non-volitional body movement. In an embodiment, the method can further include detecting a non-volitional eye movement.

Sensors

Ear-wearable devices as well as medical devices herein can include one or more sensor packages (including one or more discrete or integrated sensors) to provide data. The sensor package can comprise one or a multiplicity of sensors. In some embodiments, the sensor packages can include one or more motion sensors (or movement sensors) amongst other types of sensors. Motion sensors herein can include inertial measurement units (IMU), accelerometers, gyroscopes, barometers, altimeters, and the like. The IMU can be of a type disclosed in commonly owned U.S. patent application Ser. No. 15/331,230, filed Oct. 21, 2016, which is incorporated herein by reference. In some embodiments, electromagnetic communication radios or electromagnetic field sensors (e.g., telecoil, NFMI, TMR, GMR, etc.) sensors may be used to detect motion or changes in position. In some embodiments, biometric sensors may be used to detect body motions or physical activity. Motions sensors can be used to track movement of a patient in accordance with various embodiments herein.

In some embodiments, the motion sensors can be disposed in a fixed position with respect to the head of a patient, such as worn on or near the head or ears. In some embodiments, the operatively connected motion sensors can be worn on or near another part of the body such as on a wrist, arm, or leg of the patient.

According to various embodiments, the sensor package can include one or more of an IMU, and accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS), a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter or oxygen saturation sensor (SpO2), a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of an ear-wearable device. However, in some embodiments, the sensor packages can include one or more additional sensors that are external to an ear-wearable device. For example, various of the sensors described above can be part of a wrist-worn or ankle-worn sensor package, or a sensor package supported by a chest strap. In some embodiments, sensors herein can be disposable sensors that are adhered to the device wearer ("adhesive sensors") and that provide data to the ear-wearable device or another component of the system.

Data produced by the sensor(s) of the sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor (such as a blood oximetry sensor) can be, for example, an optical sensor, an infrared sensor, a visible light sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that the sensor package can include one or more sensors that are external to the ear-wearable device. In addition to the external sensors discussed hereinabove, the sensor package can comprise a network of body sensors (such as those listed above) that sense movement of a multiplicity of body parts (e.g., arms, legs, torso). In some embodiments, the ear-wearable device can be in electronic communication with the sensors or processor of another medical device, e.g., an insulin pump device or a heart pacemaker device.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein. Any of the methods or embodiments disclosed herein can be combined with any of the other methods or embodiments disclosed herein unless the context dictates otherwise.

The invention claimed is:

1. An ear-wearable device comprising:
- a control circuit;
- a microphone, wherein the microphone is in electrical communication with the control circuit;
- a motion sensor, wherein the motion sensor is in electrical communication with the control circuit; and
- a power supply circuit, wherein the power supply circuit is in electrical communication with the control circuit;

wherein the ear-wearable device is configured to:
- monitor signals from the microphone and/or the motion sensor to detect a pattern or patterns indicative of an occurrence of an anoxic or hypoxic neurological injury, the pattern comprising the content of an ear-wearable device wearer's speech;
- upon detecting the pattern, start a time clock period;
- during the clock period, monitor signals from the microphone and/or the motion sensor to detect a recurrence of the pattern.

2. The ear-wearable device of claim 1, the pattern comprising words indicating confusion.

3. The ear-wearable device of claim 1, the pattern comprising speech patterns of an ear-wearable device wearer's speech.

4. The ear-wearable device of claim 1, the pattern comprising long delays.

5. The ear-wearable device of claim 1, the pattern comprising the clarity of an ear-wearable device wearer's speech.

6. The ear-wearable device of claim 5, wherein clarity includes at least one of breathiness, pitch change, vowel instability, and roughness.

7. The ear-wearable device of claim 1, the pattern comprising slurred words.

8. The ear-wearable device of claim 1, the pattern comprising changed pronunciation.

9. The ear-wearable device of claim 1, wherein the ear-wearable device is configured to query an ear-wearable device wearer if a pattern indicative of an occurrence of an anoxic or hypoxic neurological injury is detected.

10. The ear-wearable device of claim 9, wherein the ear-wearable device is configured to evaluate a nature or quality of a response from the ear-wearable device wearer in response to the query.

11. The ear-wearable device of claim 1, wherein the ear-wearable device is configured to generate an alert if an occurrence of an anoxic or hypoxic neurological injury is detected.

12. The ear-wearable device of claim 1, wherein the ear-wearable device is configured to initiate the administration of a therapy if a pattern of an occurrence of an anoxic or hypoxic neurological injury is detected.

13. The ear-wearable device of claim 12, wherein initiating the administration of a therapy comprises sending a command to a drug delivery device.

14. The ear-wearable device of claim 1, wherein the ear-wearable device is configured to mark the time of first detection of a pattern indicative of an occurrence of an anoxic or hypoxic neurological injury and subsequently transmit the same for receipt by a care provider.

15. The ear-wearable device of claim 1, wherein the ear-wearable device is further configured to log an occurrence of an anoxic or hypoxic neurological injury and take a corrective action upon detecting the recurrence of the pattern.

16. The ear-wearable device of claim 1, wherein the ear-wearable device is further configured to not log an occurrence of an anoxic or hypoxic neurological injury upon not detecting the recurrence of the pattern.

17. An ear-wearable device comprising:
- a control circuit;
- a microphone, wherein the microphone is in electrical communication with the control circuit;
- a motion sensor, wherein the motion sensor is in electrical communication with the control circuit; and a power supply circuit, wherein the power supply circuit is in electrical communication with the control circuit;

wherein the ear-wearable device is configured to:

monitor signals from the microphone and/or the motion sensor to detect a pattern or patterns indicative of an occurrence of an anoxic or hypoxic neurological injury;

upon detecting the pattern, monitor signals from the microphone and/or the motion sensor to detect a recurrence of the pattern during a time clock period.

* * * * *